US00RE45177E

(19) United States
(12) Reissued Patent
Galvanauskas et al.

(10) Patent Number: US RE45,177 E
(45) Date of Reissued Patent: Oct. 7, 2014

(54) QUASI-PHASE-MATCHED PARAMETRIC CHIRPED PULSE AMPLIFICATION SYSTEMS

(75) Inventors: Almantas Galvanauskas, Ann Arbor, MI (US); Donald Harter, Ann Arbor, MI (US); Gregg Sucha, Manchester, MI (US)

(73) Assignee: IMRA America, Inc., Ann Arbor, MI (US)

(21) Appl. No.: 10/396,815

(22) Filed: Mar. 26, 2003

Related U.S. Patent Documents

Reissue of:
(64) Patent No.: 6,208,458
Issued: Mar. 27, 2001
Appl. No.: 09/116,241
Filed: Jul. 16, 1998

U.S. Applications:
(63) Continuation-in-part of application No. 08/822,967, filed on Mar. 21, 1997, now Pat. No. 6,181,463.

(51) Int. Cl.
*H01S 3/10* (2006.01)
*H01S 3/091* (2006.01)

(52) U.S. Cl.
USPC ..... 359/345; 359/330; 359/332; 359/340

(58) Field of Classification Search
USPC ..... 359/333, 345, 330, 332, 340; 216/65
See application file for complete search history.

(56) References Cited

U.S. PATENT DOCUMENTS 5,321,718 A * 6/1994 Waarts et al. ..... 372/108
5,499,256 A * 3/1996 Bischel et al. ..... 372/28
5,640,480 A * 6/1997 Komine ..... 385/122
5,720,894 A * 2/1998 Neev et al. ..... 216/65
5,787,102 A * 7/1998 Alexander et al. ..... 372/22
5,909,306 A 6/1999 Goldberg et al.
6,151,338 A 11/2000 Grubb et al.
6,181,463 B1 1/2001 Galvanauskas et al.
2002/0172481 A1 11/2002 Kubota et al.
2003/0065312 A1 4/2003 Owa et al.

OTHER PUBLICATIONS

M.A. Arbore et al, "Frequency doubling of femtosecond erbium-fiber soliton lasers in periodically poled lithium niobate", Optics Letters, vol. 22, No. 1, Jan. 1, 1997, pp. 13-15.

(Continued)

*Primary Examiner* — Mark Hellner
(74) *Attorney, Agent, or Firm* — Sughrue Mion, PLLC; Richard C. Turner

(57) ABSTRACT

Use of quasi-phase-matched (QPM) materials for parametric chirped pulse amplification (PCPA) substantially reduces the required pump peak power and pump brightness, allowing exploitation of spatially-multimode and long duration pump pulses. It also removes restrictions on pump wavelength and amplification bandwidth. This allows substantial simplification in pump laser design for a high-energy PCPA system and, consequently, the construction of compact diode-pumped sources of high-energy ultrashort optical pulses. Also, this allows elimination of gain-narrowing and phase-distortion limitations on minimum pulse duration, which typically arise in a chirped pulse amplification system. One example of a compact source of high-energy ultrashort pulses is a multi-mode-core fiber based PCPA system. Limitations on pulse energy due to the limited core size for single-mode fibers are circumvented by using large multimode core. Limitations on pulse duration and beam quality due to multimode core are circumvented by using a PCPA scheme. Additionally, the large core of the multimode fiber facilitates cladding-pumping by inexpensive and high-power multiple-mode laser diodes.

14 Claims, 14 Drawing Sheets

(56) References Cited

OTHER PUBLICATIONS

A. Galvanauskas et al, "Fiber-laser-based femtosecond parametric generator in bulk periodically poled $LiNbO_3$", Optics Letters, vol. 22, No. 2, Jan. 15, 1997, pp. 105-107.
M.A. Arbore, et al, "Engineerable compression of ultrashort pulses by use of second-harmonic generation in chirped-period-poled lithium niobate", Optics Letters, vol. 22, No. 17, Sep. 1, 1997, pp. 1341-1343.
Myers et al, J. Opt. Soc. Am., vol. 12, No. 11, Nov. 1995, pp. 2102-2116, Nov. 1995.*
Lovering et al, Optics letters, vol. 21, #18, pp. 1439-1441, abstract only herewith, Sep. 15, 1996.*
Galvanauskas et al, CLRO '96, pp. 495-496 abst. only herewith, May 28, 1996.*
Galvanauskas et al, Ultrafast Phenamena, vol. 8, pp. 471. Abstract only herewith, Jun. 1, 1996.*
A. Galvanauskas et al, "Parametric chirped pulses micro-amplifier based on engineerable quasi-phas-matched $LiNbO_3$" CLEO 1998, Technical Digest CME2, p. 16.
A. Galvanauskas et al, "Chirped-pulse-amplification circuits for fiber amplifiers, based on chirped-period quasi-phase-matching gratings", Optics Letters, vol. 23, No. 21, Nov. 1, 1998, pp. 1695-1697.

* cited by examiner

QUASI-PHASE-MATCHED PARAMETRIC CHIRPED PULSE AMPLIFICATION SYSTEMS

Matter enclosed in heavy brackets [ ] appears in the original patent but forms no part of this reissue specification; matter printed in italics indicates the additions made by reissue.

This is a Continuation-in-Part of U.S. application Ser. No. 08/822,967 filed Mar. 21, 1997.

BACKGROUND OF THE INVENTION

The invention relates to methods and apparatus for converting optical pulses generated by compact, low-intensity long-pulse pump sources, such as diode, fiber or solid-state lasers, into high-energy ultrashort optical pulses through the use of optical parametric amplifying media, and to particular applications of the same.

As used herein, the term "high-energy pulses" refers to optical pulses having energy levels higher than that obtainable directly from ultrashort-pulse oscillators. Typically, compact mode-locked oscillators produce pulses with maximum energies at the 10 nJ level. Therefore, pulses with energies of more than 10 nJ are defined herein as high-energy pulses.

Ultrashort pulse lasers and amplifiers belong to a particular class of laser devices which generate ultimately short optical pulses (at the optical-wavelength limit) with durations in the femtosecond ($10^{-15}$s) to picosecond ($10^{-12}$s) regimes. The applications of such pulses are determined by their characteristic features, which include short duration, high peak power and high spatial and temporal coherence. As described in more detail below, advantageous use can be made of such pulses in fields such as machining, medicine (surgical applications including tissue ablation, tissue removal, precise incisions, sclera and skin surgery, intraocular surgery and molecular surgery), LIDAR, scientific measurement and imaging.

Diode lasers are compact sources of laser emission which possess two unique technological advantages. First, diode lasers provide direct conversion from electrical to optical power with high efficiency. Second, they are monolithic devices with small dimensions (typically less than 1 mm). Consequently, their parameters such as size, robustness, reliability, life-time, manufacturability and cost are substantially better than corresponding parameters of other laser structures, such as gas, dye or bulk solid-state lasers. These key features make them ideally suitable for developing commercially viable laser sources. However, direct use of diode lasers in the generation of high-energy ultrashort pulses is limited. Essentially this is determined by the small cross-sectional area of a single-mode diode. Catastrophic damage to the diode and severe nonlinear distortions of the ultrashort pulses restricts obtainable peak intensities. Additionally, due to the same small cross-sectional area, stored energy and saturation fluency are also limited. Maximum energies directly obtainable from a laser diode are limited to about 100 pJ, which is at the lower limit of practically significant ultrashort pulse energies. While the effective cross-sectional area of a laser diode can be increased by resorting to multiple-transversal-mode structures or multiple-stripe structures, the requirement of spatial and temporal coherence does not permit direct generation of ultrashort pulses with such devices.

This necessitates using diodes as pump sources for other classes of ultrashort-pulse lasers and amplifiers in order to develop practical systems. Rare-earth doped fiber lasers represent one such class of devices and are closest to semiconductor gain media in compactness, as mainly determined by the small transverse dimensions of the fiber. The typical diameter of a fiber structure is less than 1 mm. Unlike a semiconductor laser, a fiber laser can have a length of several meters, but due to the small transverse dimensions it can be spooled to occupy a small space. In effect, the fiber laser is a one dimensional structure, with the transverse distribution of the optical field being the same at any longitudinal position. Rare-earth doped fibers can be diode-laser pumped. For example, known Er-doped fiber laser systems have been pumped with existing high-power laser diodes emitting at 1480 nm or 980 nm.

As reported in Broad-area Diode-pumped 1 W Femtosecond Fiber System, a. Galvanauskas, M. E. Fermann, D. Harter, J. D. Minelly, G. G. Vienne, J. e. Caplen, Conference on Lasers and Electro-Optics, vol. 9 1996 OSA Technical Digest Series (Optical Society of America, Washington, D.C., 1996) pp. 495, hereby incorporated herein by reference, high power multimode diode pump light is efficiently converted into a high power ultrashort pulse output by fiber cladding-pumping techniques and chirped pulse amplification. In general, chirped pulse amplification is necessary for any quantum amplifier in order to extract the maximum available energies without incurring nonlinear distortion of the ultrashort pulses or optical damage to optical components or the gain medium. Typically, the peak intensity of an ultrashort pulse, with an energy equal to the saturation energy, is higher than the saturation fluency of the medium.

However, in order to preserve spatial and temporal coherence and to sustain ultrashort pulses, the fiber output has to be single-mode. This puts constraints on the fiber core size and, consequently, on the maximum obtainable pulse energies and peak intensities, for reasons here equivalent to the case of a single-mode semiconductor laser. Maximum obtainable energies for a single-mode fiber, however, are substantially higher than for a semiconductor. The maximum, saturation-fluency-limited energies have already been experimentally produced with some diode pumped Er-fiber chirped pulse amplification systems, yielding pulse energies of more than 10 μJ after amplification and recompression. However, for a variety of practical applications, such as micromachining, optical surgery, etc. much higher ultrashort pulse energies are required (typically in the range of 1 to 10 mJ). To obtain these pulse energies, bulk quantum amplifiers have been conventionally used. In a bulk medium, the beam size is substantially larger than the single-mode guided beam in a fiber or a semiconductor structure, alleviating the problem of high peak intensities. Furthermore, certain solid-state gain media have properties which permit design of compact devices. However, a number of limitations, as determined by the general properties of quantum amplifiers, make it practically difficult to implement compact solid-state designs for direct amplification of ultrashort high-energy pulses. This is revealed by considering the general properties of a quantum amplifier.

A quantum amplifier stores pump energy in an upper level of an optical transition state, which can be harvested by a passing signal through the action of optical stimulated emission. Known solid-state ultrashort-pulse amplifying arrangements include single or multiple-pass energies in the 1 μJ to 1 J range. Chirped pulse amplification is a necessity for these systems.

However, bulk lasers and amplifiers have notable limitations. First, solid-state lasers and amplifiers are substantially larger and more expensive than their semiconductor and fiber counterparts. The size and cost are mainly driven by the cumbersome pump sources required, e.g., high-power Ar lasers or lamps. Diode pumping is possible for few such systems. It is necessary to pump a quantum amplifier within the fixed absorption band of the particular gain medium. For many media, this eliminates or restricts diode-laser pumping, because reliable and high-power pump diodes are currently available at only a few wavelengths. For example, the most popular solid-state medium for ultrashort pulse generation is Ti-sapphire, which can not be directly diode laser pumped.

Second, quantum amplifiers have a limited gain bandwidth, which is determined by the width of the optical transition in the particular gain medium. The narrow width of the gain bandwidth substantially limits the use of certain materials for amplifying ultrashort pules.

Third, intrinsic properties of the gain medium, such as the lifetime of the excited optical transition and the simulated emission cross-section, set limits on the maximum extractable average power and pulse energy from a particular quantum amplifier.

Fourth, at high power levels, bulk amplifiers are susceptible to thermal effects which change the optical properties of the gain medium. This makes the operation of such devices sensitive to changes in the environment.

An alternative approach for achieving optical amplification is to employ optical parametric amplification (OPA) in a nonlinear material. According to the OPA approach, pump energy is not stored in the material but directly transferred from the pump into the signal; the nonlinear material only mediates the process. Pulse distortions through phase distortion can in general be avoided because the second-order nonlinearity is much stronger than the third order (responsible for self or cross-phase modulation). The maximum obtainable energy is essentially limited by the damage threshold of the particular material. The required pump wavelength and the available amplification bandwidth are determined by the fundamental optical properties of the particular crystal, such as orientation and size of the refractive index ellipsoids at the interacting wavelengths in conventional birefringence phase-matching. These fundamental optical properties also determine the useful crystal orientation and, consequently, the magnitude of the nonlinearities which can be utilized. In practice, this puts limitations on the pump wavelengths and bandwidths accessible with the available nonlinear materials and, in general, leads to the high energies required to pump such amplifiers. As a result of the above limitations, parametric interaction at present is generally used as a means of converting the wavelength of an optical signal, not as a means of energy amplification.

In Powerful femtosecond Pulse Generating Chirped and Stretched Pulse Parametric Amplification in BBO Crystals, A. Dubietis, G. Jonusauskas, and A. Piskarskas, Opt. Comm. 88, 437 (1992), hereby incorporated herein by reference, it is suggested that high-energy ultrashort optical pulses may be obtained through the use of optical parametric amplifiers instead of conventional quantum amplifiers. The article teaches that ultrashort optical pulses must be stretched to match the duration of the pump pulse for efficient energy transfer from the pump into the signal. This work demonstrated 1:30 conversion from a 3 mJ pump at 0.53 μm into a 100 μJ signal at 1.06 μm with short (about 5 ps) stretched pump pulses.

However, the work of Dubietis et al. does not teach energy conversion from low to high brightness beams, nor how to achieve a compact source of high-energy ultrashort pulses through the use of compact pump sources, such as diode, fiber or microchip lasers. (One of the problems that would be encountered is that to demonstrate the same conversion efficiency with longer pump pulses (in the nanosecond range), pulse energies would have to be increased proportionally by a factor of about 100 (into the Joule range). At present it is difficult to get such high energies from compact pulse sources.) Also, this work does not remove the limitations on the pump wavelength and the gain bandwidth of an ultrashort-pulse amplifier. Additionally, in this work, both the pump and amplified pulses were from the same laser source. No method of synchronizing long-pulse pump and short pulse sources is suggested. It is problematic to synchronize pulses from a conventional Q-switched pump laser with ultrashort pulses from a mode-locked source.

Although the foregoing primarily stresses the use of diode lasers as pump sources, it is axiomatic that the pump source may be formed of a combination of a diode laser and one or more serially arranged laser sources at least the first stage of which is capable of being diode-laser pumped. For example, the pump source may be constituted of a diode laser which pumps a rare-earth fiber laser or a Q-switched pulse source.

SUMMARY OF THE INVENTION

It is the main object of the present invention to provide compact amplifiers of high energy ultrashort optical pulses.

It is a further object of the present invention to provide ultrashort-pulse amplifiers without limitations on pumping wavelength and amplification bandwidth.

It is another object of the present invention to utilize compact cw or pulsed pump sources, such as diode, fiber or solid-state lasers and combinations of same, to efficiently pump optical parametric amplifiers for ultrashort-pulse amplification. A further object of the invention is to utilize multi-spatial mode compact sources, such as broad-area diodes or diode arrays, multimode-core fiber lasers and amplifiers, microchip laser arrays or other multimode solid-state lasers, to parametrically amplify a diffraction-limited single-mode beam.

It is also an object of the present invention to provide methods and means for proper timing of the pump and stretched ultrashort pulses in order to overlap them temporally in a parametric gain medium.

It is an additional object of the invention to utilize the disclosed laser devices in a variety of scientific, medical and industrial applications, in combination with application—specific systems designed to make optimal use of the laser pulses produced by the laser devices described above.

According to one aspect of the present invention, a quasi-phase-matched nonlinear material is used as a parametric gain medium for parametric chirped pulse amplification (QPM PCPA) of ultrashort pulses. The phase-matching properties of a QPM material are tailored during the fabrication process, which essentially enables the removal of limitations on the pump wavelengths and achievable gain bandwidths. Furthermore, the ability to tailor the phase-matching properties allows the selection of advantageous crystal geometries, which enables an increase in the interaction length by eliminating spatial beam walk-off and utilization of the highest nonlinear coefficients available in a particular optical material. As a result, the pump energies required to achieve high conversion efficiency and high gain in a QPM parametric amplifier can be substantially reduced as compared to a conventional parametric amplifier. It also facilitates conversion of a multimode pump beam into a diffraction-limited signal beam. In general, this allows efficient utilization of relatively long and multimode pump pulses, which can be obtained using a variety of relatively simple and compact diode-pumped sources. This is not possible using conventional nonlinear crystals as described in Dubietis et al.

According to a broader aspect of the invention, a general method of converting the cw or pulsed power of single-mode or multimode laser diodes into the amplified energy of ultrashort optical pulses is described. In general, this conversion is accomplished in two basic steps. First, diode-laser power is converted, either directly or through the use of one or more other laser media, into a high-energy pump pulse of proper duration to match that of a stretched signal pulse. The stretched signal pulse is produced from an ultrashort pulse by means of a pulse stretcher. Second, the stretched signal is amplified parametrically in a nonlinear crystal pumped by the pump signal pulses. Under certain conditions, the parametric amplifier will provide undistorted amplification of a diffraction-limited single-mode beam even for the spatially multimode pump beam. The amplified signal is finally recompressed back to ultrashort duration using a pulse compressor.

The parametric chirped pulse amplification (PCPA) technique thus enables conversion of energy from long, nanosecond pulses into short, femtosecond pulses in a simple and efficient way. High energy long pulses for pumping PCPA systems are always much easier to produce than femtosecond pulses of comparable energy. Requirements on bandwidth, nonlinear distortion threshold, beam quality, etc. are much relaxed.

Although, in principle, any standard Q-switched laser could be employed to pump the femtosecond PCPA system, in order to achieve optimum performance of PCPA (in terms of power efficiency, optical damage issues, etc.) it is necessary to design specific nanosecond-pump laser systems.

The present invention therefore further includes designs of compact arrangement for pumping the parametric amplifier, including multimode-core fibers and microchip solid-state lasers and arrays.

DETAILED DESCRIPTION OF THE PREFERRED EMBODIMENTS

Figure 1:
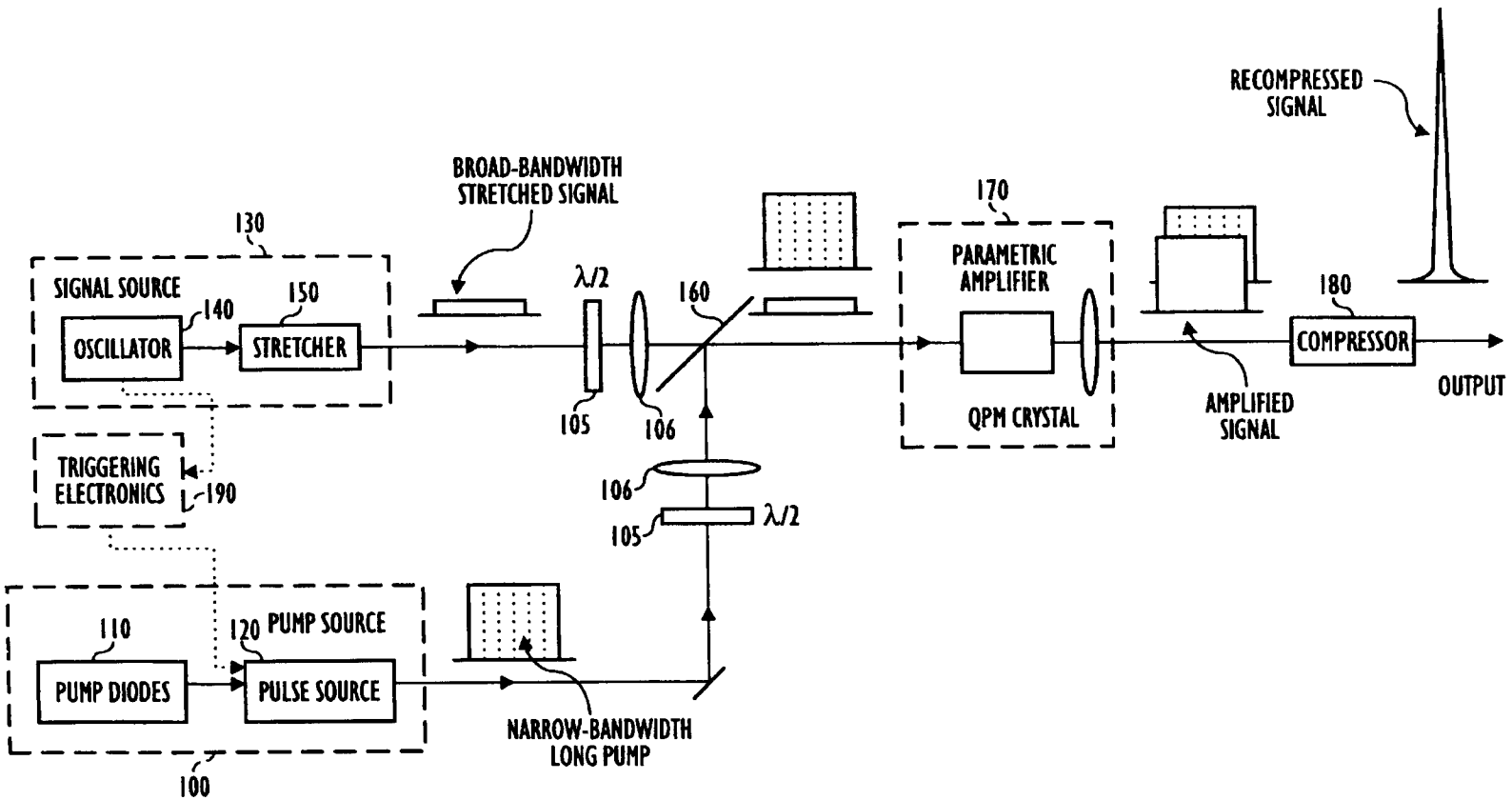
FIG. 1 depicts the arrangement of an amplification system according to a general embodiment of the present invention.

FIG. 1 illustrates the arrangement of a general embodiment of an amplification system according to the present invention. As shown in FIG. 1, the amplification system includes a pump source 100 having pump diodes 110 for pumping a high energy pulse source 120. The signal source 130 includes an oscillator 140 generating ultrashort pulses, and a pulse stretcher 150. A beamsplitter 160 is used for combining the high-energy pump pulses and the stretched ultrashort pulses. The combined signals are applied to the parametric amplifier 170, and the amplified signal is applied to pulse compressor 180. Other components for implementing the system include waveplates 105 for setting the polarization states required for efficient nonlinear interactions, and appropriate focusing optics 106. Triggering electronics 190 are provided to pump signal pulses and stretched signal pulses are overlapped temporally and spatially in the nonlinear crystal of the parametric amplifier 170.

The use of parametric amplification provides several important advantages. First, it allows exploitation of multimode and long-pulse pump sources. In general, such sources are much less complicated and provide substantially higher energies than compact sources for direct ultrashort pulse generation and amplification.

Second, limitations on the gain bandwidth and pump wavelength, inherent in quantum amplifiers, are completely removed by using quasi-phase-matched nonlinear materials. Using chirped-period quasi-phase-matched bulk materials, the gain bandwidth can be engineered to be of any required width. The pump wavelength is selected by the proper quasi-phase-matching period of the parametric amplifier. When appropriate, the pump wavelength can be converted to be shorter than the amplified signal by using second-harmonic generation.

Third, parametric amplification systems are inherently simpler and more compact. Parametric amplification in a single stage can provide up to about 90 dB gain (the limit is imposed only by the threshold for optical parametric generation (OPG)). Therefore, starting from about 10 pJ, as a minimum energy obtainable with any fiber, laser diode or solid state oscillator, high pulse energies in the 1 mJ to 1 J range can be reached using only one or two amplification stages. Consequently, regenerative schemes and multipass schemes are not necessary.

In order for such an amplification system to be practical, the parametric gain and the maximum energy conversion from the pump into the signal in a parametric amplifier must be sufficiently high (approximately 10 to 50%). This conversion is determined by the peak intensity of the pump and the properties of the nonlinear crystal. For birefringent phase-matched crystals, such conversion requires very high peak intensities, which are substantially higher than those practically achievable with a multimode or single-mode nanosecond duration pump pulse form a compact, diode-pumped source (>100 mJ). According to the present invention, using novel quasi-phase-matched (QPM) materials, such as periodically poled lithium niobate (PPLN), lower-intensity and low-brightness nanosecond output from a diode-laser pumped compact source can be successfully used for efficient parametric amplification of stretched ultrashort pulses. For a further discussion of PPLN and related materials and their properties, the reader is referred to the following sources, which are each herewith incorporated by reference herein: U.S. application Ser. No. 08/824,032, filed Mar. 21, 1997 (Arbore et al., Stanford University Docket No. S96-208): U.S. application Ser. Nos. 08/763,381 and 08/789,995, which disclose the use of PPLN crystals in pulse amplification system; and Myers et al., "Quasi-phase-matched optical parametric oscillators in bulk periodically poled lithium niobate", J. Opt. Soc. Am. B, 22, 2102 (1995).

In contrast to traditional chirped pulse amplification schemes, where ultrashort pulses are stretched in order to eliminate nonlinear effects, this approach requires stretching ultrashort pulses solely for the purpose of maximizing extraction efficiency from the long pump pulse. In general, the use of longer pump and stretched pulses will provide higher amplified pulse energies for a given pump pulse peak intensity. The maximum useable pump pulse duration is determined by the damage threshold of the nonlinear crystal and by the maximum recompressable pulse width for amplified seed pulses. For example, in order to keep the pump intensities below the damage threshold in PPLN, a pump pulse duration below 500 ps preferably should be used. Also, existing pulse stretcher and compressor designs limit the stretched pulse duration to a nanosecond scale. This restricts potentially useful pump pulse duration to within the range of 100 ps to a few nanoseconds. Such pulses can be obtained with a variety of passively or actively Q-switched or Master-Oscillator-Power-Amplifier (MOPA) systems, such as laser-diode pumped Nd:YAG or alexandrite systems, compact laser-diode pumped microlasers, or amplified fiber systems. Pump energies that can be provided are in the range from 1 μJ to more than 1 J, allowing for the amplified signal pulses in the same range.

The oscillator 140 can be a mode-locked laser, a gain switched, or a fast-frequency-modulated semiconductor laser. In the latter case, the oscillator can produce stretched pulses directly, thus eliminating the need for a pulse stretcher.

A variety of different devices known in the prior art are suitable for use as pulse stretcher 150 and compressor 180. For example, diffraction-grating based devices, fiber gratings or hybrid combinations (e.g., a fiber or fiber-grating as a stretcher and a diffraction grating pair as a compressor) can be used. In general, however, the maximum stretched pulse durations from existing practical pulse stretchers are limited to approximately a nanosecond range. To maximize parametric amplification efficiency and minimize deleterious effects, such crystal damage, pump pulse durations should match that of the signal pulse. Consequently, for the present invention, the most relevant pump pulse durations encompass nanosecond and subnanosecond ranges.

It is an important aspect of the invention that the practical advantages of the amplification scheme are essentially determined by the advantageous properties of the pump pulse sources used. Because a quasi-phase-matched parametric medium allows a reduction of required pump energies, increased pulse lengths, and use of multimode pump beams, a variety of practical pump sources becomes available for implementation. The present invention thus includes particular embodiments based on different pump sources.

Output device 181 is shown in FIG. 1 as the recipient of the laser output beam. As described below, this device can be one of many beam utilization devices, such as a laser surgical instrument, a workpiece machining system, etc. Although represented in FIG. 1 for purposes of convenience, it will be apparent that the beam utilization device could be connected to the output of any of the other embodiments of the invention, and is shown only in FIG. 1 simply as exemplitive.

Figure 2:
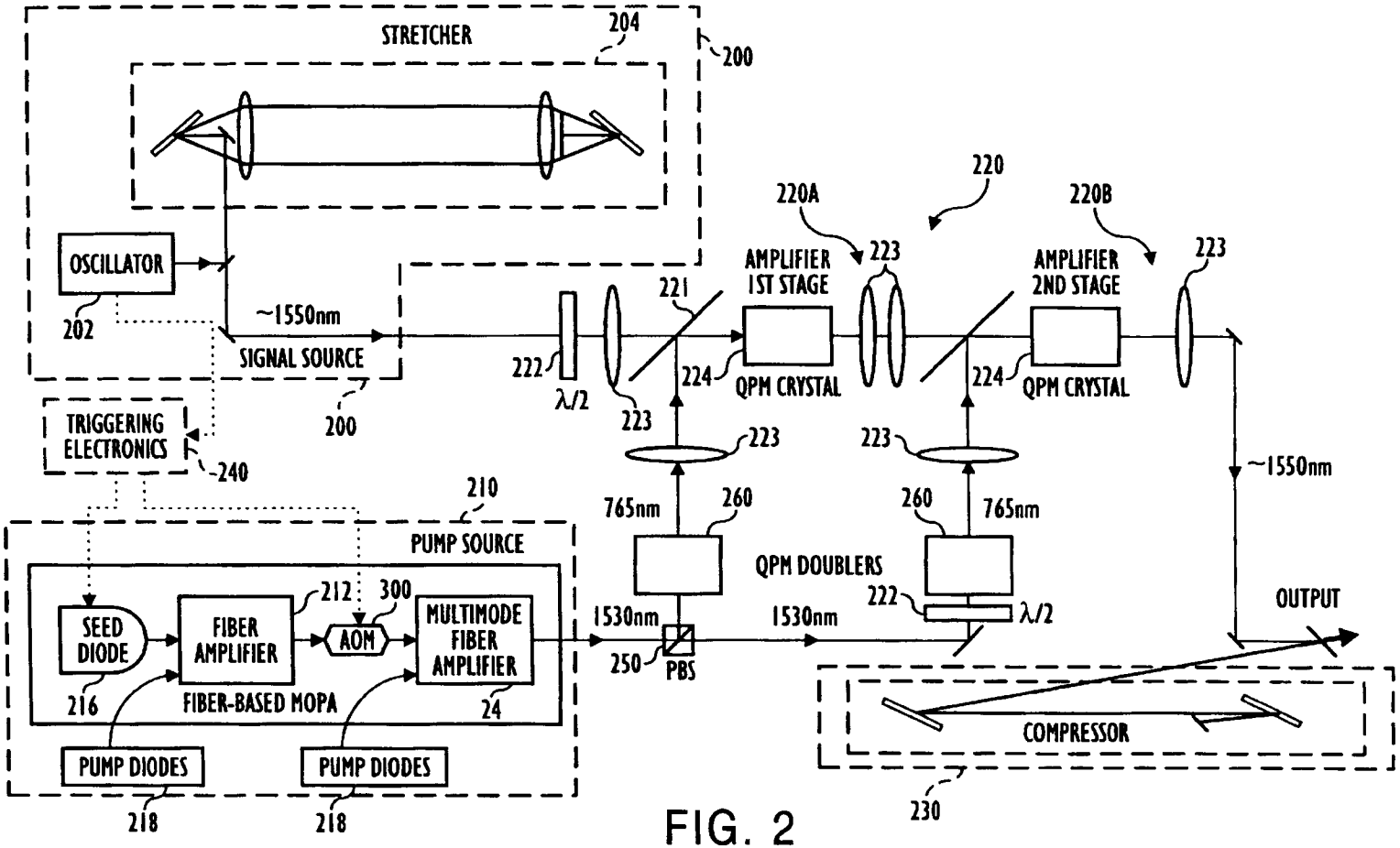
FIG. 2 depicts a multimode-fiber based PCPA system according to a first embodiment of the present invention.

According to a first exemplary embodiment shown in FIG. 2, the present invention is implemented as a multimode-fiber based parametric chirped pulse amplification (PCPA) system.

Use of a fiber gain medium in a PCPA system involves the following considerations. As discussed above, the small transverse dimensions of a fiber gain medium sets the limitations on the maximum pulse energy. For a signal to be single-mode (have a gaussian spatial distribution at the output of the fiber), the maximum cross-sectional diameter of the fiber core is about 15 μm. Larger diameter single-mode core would require an unrealistically small refractive-index difference between the core and the cladding, and would also cause intolerably high bending losses. For Er-doped fiber gain medium, this sets the maximum obtainable pulse energy at approximately the 100 μJ level.

Resorting to multimode fiber amplifiers, it is possible to use substantially larger core diameters. With 30 μm to 100 μm core diameter multimode amplifiers, it is possible to reach pulse energies in the range from 100 μJ to 10 mJ. However, use of multimode fiber amplifiers for conventional chirped pulse amplification of femtosecond pulses is practically excluded by high inter-mode dispersion (from approximately 1 to 10 ps/m), which causes severe temporal distortions of recompressed pulses. Another essential disadvantage for directly generating ultrashort pulses with a multimode fiber is the non-gaussian profile of the multimode beam, which substantially reduces the brightness and spatial coherence of the beam.

These limitations of multimode fiber amplifiers can be overcome by using multimode fiber as a pump for a parametric amplifier of stretched ultrashort pulses rather than for direct chirped pulse amplification.

As shown in FIG. 2, a multimode-fiber based PCPA system includes a signal source 200 providing stretched ultrashort pulses, a pump source 210 providing long high-energy pump pulses, a parametric amplifier 220, a pulse compressor 230 and triggering electronics 240 synchronizing the pump and amplified signals.

The signal source 200 comprises a mode-locked oscillator 202 (e.g., a mode-locked fiber oscillator) and a pulse stretcher 204. Alternatively, the signal source may comprise a first-tuned laser diode directly generating broad-bandwidth stretched pulses (not shown). A variety of possible stretcher and compressor arrangements are available, as discussed above.

The pump source 210 comprises multistage or multipass fiber amplifiers 212 and 214, seeded by a laser diode 216 and pumped by pump diodes 218. Pumping the seed diode 216 with triggering electronics 240, e.g., a standard electric pulse generator, the optical seed pulses can be tailored to any duration starting from about 100 ps and longer. The master-oscillator-power-amplifier schemes (MOPA) allows generation of pump pulses of any required length and at a required repetition rage. Importantly, this scheme allows synchronization of pump pulses to the stretched ultrashort pulses with negligible jitter. For example, a nanosecond electric pulse generator can be triggered through a fast photodiode by the train of the ultrashort pulses. Timing jitter of the produced pump pulses with respect to the stretched pulses can be less than 30 ps, which is only a fraction of the duration of the pump pulses.

Figure 3A:
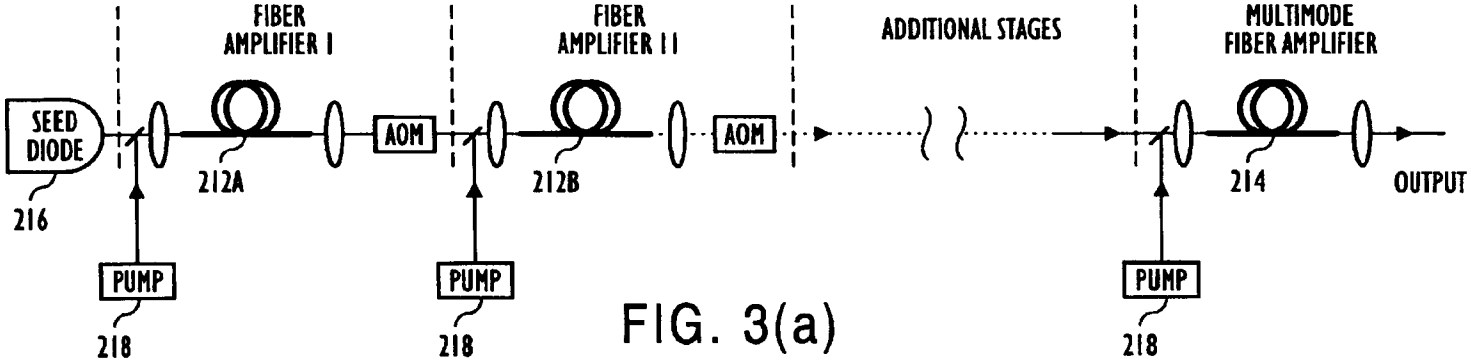
FIG. 3(a) depicts an example of a pump source using cascaded linear amplification.

Multipass or multistage fiber amplifiers are necessary in the pump source to provide up to 90 dB of gain to reach millijoule pulses starting from a typical~10 pJ output from a laser diode 216. Typical single-pass gain in an Er-doped fiber amplifier is 20-30 dB. Consequently, 4 to 5 amplification stages are needed to reach the desired energy levels. A conceptual example using cascaded linear amplifiers is shown in FIG. 3(a). Acousto-optic modulators 300 between the stages are necessary to prevent cross-saturation between the stages due to amplified spontaneous emission (ASE). The whole chain can be comprised of multimode fibers. Alternatively, single-mode fibers may be used in the first stages, where pulse energy is still low, and multimode amplifiers are used only in the last stage or stages. For the last stage, it is advantageous to use highly doped fibers for minimizing the length and the nonlinear effects in the core. Nonlinear effects reduce the amplifiers' efficiency and cause spectral broadening of the pump pulse, which is undesirable for pumping nonlinear crystals.

Figure 3B:
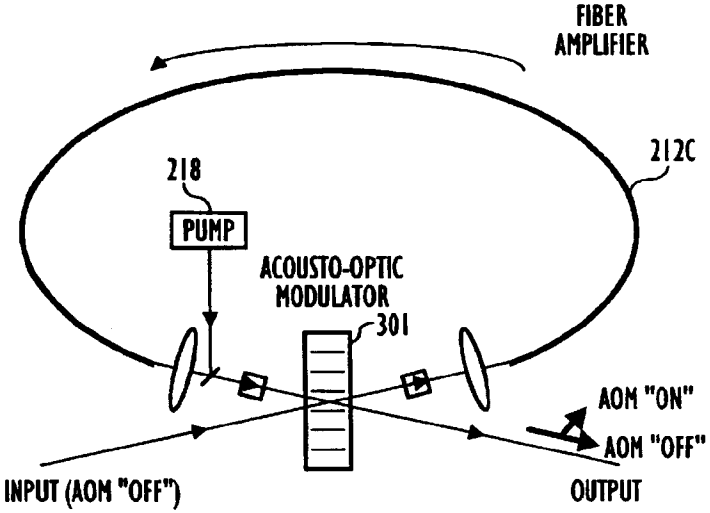
FIG. 3(b) depicts an example of a pump source using a multi-pass amplification arrangement.

The "linear" approach of cascading fiber amplifiers shown in FIG. 3(a) lacks in some economies, in that the price and size of the pump source is proportional to the number of stages. An advantageous alternative solution is to use a multiple-pass arrangement, such as the one shown in FIG. 3(b). In this case, one or a maximum of two amplification stages is sufficient. The acousto-optic modulator 301 operates as a switch which injects seed pulses into the amplifier and then directs them into the output only after the sufficient energies are reached after several passes. Typically, the modulator speed (gate width) is required to be 100-200 ns in order to match the round trip time of a typical fiber amplifier 212C (approximately 10-50 ns). Because acousto-optic modulators are, in general, polarization insensitive, both single-mode and multimode fibers can be employed for such a multiple-pass design. Due to the low average powers of a seed signal, two-stage schemes are advantageous, where one of the stages is a linear amplifier and another is a multipass amplifier.

Fiber amplifiers can be pumped by single-mode diodes, such as laser diode MOPA; however, single-mode sources are more expensive and provide comparatively lower power. Therefore, it is preferable to use multimode or multiple-diode sources. This can be implemented through double-clad geometry of both single-mode and multimode fiber amplifiers. Importantly, the large core area of a multimode-core fiber facilitates the pump absorption in cladding pumping, as compared to a double-clad single-mode-core fiber. Also, for multimode fibers with a sufficiently large core diameter (typically >100 μm) broadstripe or multimode diode lasers can be used for direct in-core pumping. In general, the use of multimode laser diodes is very advantageous in achieving very compact and robust designs of the pump source and consequently of the complete system.

The pumping wavelength of a parametric amplifier must be shorter than the signal wavelength. If fiber amplifiers, which constitute the pump source, operate at a shorter wavelength than the ultrashort pulse source, then the only requirement is to achieve the proper phase-matching in a parametric crystal by choosing the appropriate nonlinear material (e.g., selecting a suitable value for the quasi-phase-matching period in a periodically poled lithium niobate crystal). One example is a femtosecond oscillator based on Er-doped fiber (operating wavelength at 1550 nm) and a pump source using Nd-doped glass fiber (operating wavelength at 1060 nm). If both the pump and the signal source use the same type of doped fibers (e.g., both use Er-doped fiber), then it is necessary to frequency double the pump beam with QPM or other known frequency doublers 260. It is also advantageous to operate the pump source at a slightly shorter fundamental wavelength than the signal (e.g., 1530 nm and about 1560 nm, respectively) in order to avoid phase-sensitive parametric amplification at the degeneracy.

The parametric amplifier 220 consists of one or more amplification stages. It is preferable to use two stages 220A and 220B (FIG. 2). The use of a double stage rather than a single stage makes it easier to achieve over 90 dB amplification of the stretched pulses (from about 10 pJ to about 10 mJ). The maximum gain in a parametric amplifier is limited by the onset of parametric generation. This occurs in a single stage at about 90 dB gain, which is sufficient to amplify spontaneous vacuum fluctuations to the macroscopic level. Typically, the output of a multimode fiber will be unpolarized. In this case, the preferable arrangement for implementing two-stage parametric amplification includes polarizing beamsplitter 250 at the output of the pump source 2101 to produce two pump channels, i.e., one for each parametric amplification stagge 220A and 220B. This arrangement ensures the use of all the pump power.

Other components for implementing the system include dichroic mirrors 221 for combining pump and signal beams, waveplates 222 for setting the polarization states required for efficient nonlinear interactions, and appropriate focusing optics 223. The femtosecond signal should be stretched prior to the amplification to approximately the same duration as the pump pulse. The pump and signal pulses must be overlapped both in time and in space inside parametric amplifier crystal 224. To avoid crystal damage, the spot size must be sufficiently large.

The parametric crystal 224 preferably has high nonlinearity, e.g., such as in PPLN, PPLT or other quasi-phase-matched materials, in order to achieve efficient amplification with peak intensities below the damage threshold. Large spot size is also advantageous for reaching high efficiency parametric amplification using a spatially multimode pump beam. The use of a highly efficient nonlinear crystal like PPLN is essential for the realization of a fiber based system. With the currently available conventional birefringence-matched crystals, the required peak powers are intolerable even for large-core multimode fibers.

As evident from above description, use of a fiber amplifier as a pump source rather than for direct amplification of stretched femtosecond pulses eliminates the effect of intermode dispersion as well as poor beam quality of the multimode output from a high-energy fiber amplifier, and provides single-mode and transform-limited output at high pulse energies.

As described above, maximum energies obtainable scale with the size of the core of the multimode fiber. More than 10 mJ is available with about 100 μm core fiber. Taking into account frequency-doubling and parametric amplification efficiencies, 10 mJ pulses are sufficient for obtaining more than 1 mJ amplified pulses. Further, energy scaling is possible by using even larger fibers. Alternatively, output pulse energies can be scaled by combining outputs of multiple pump sources.

Figure 4A:
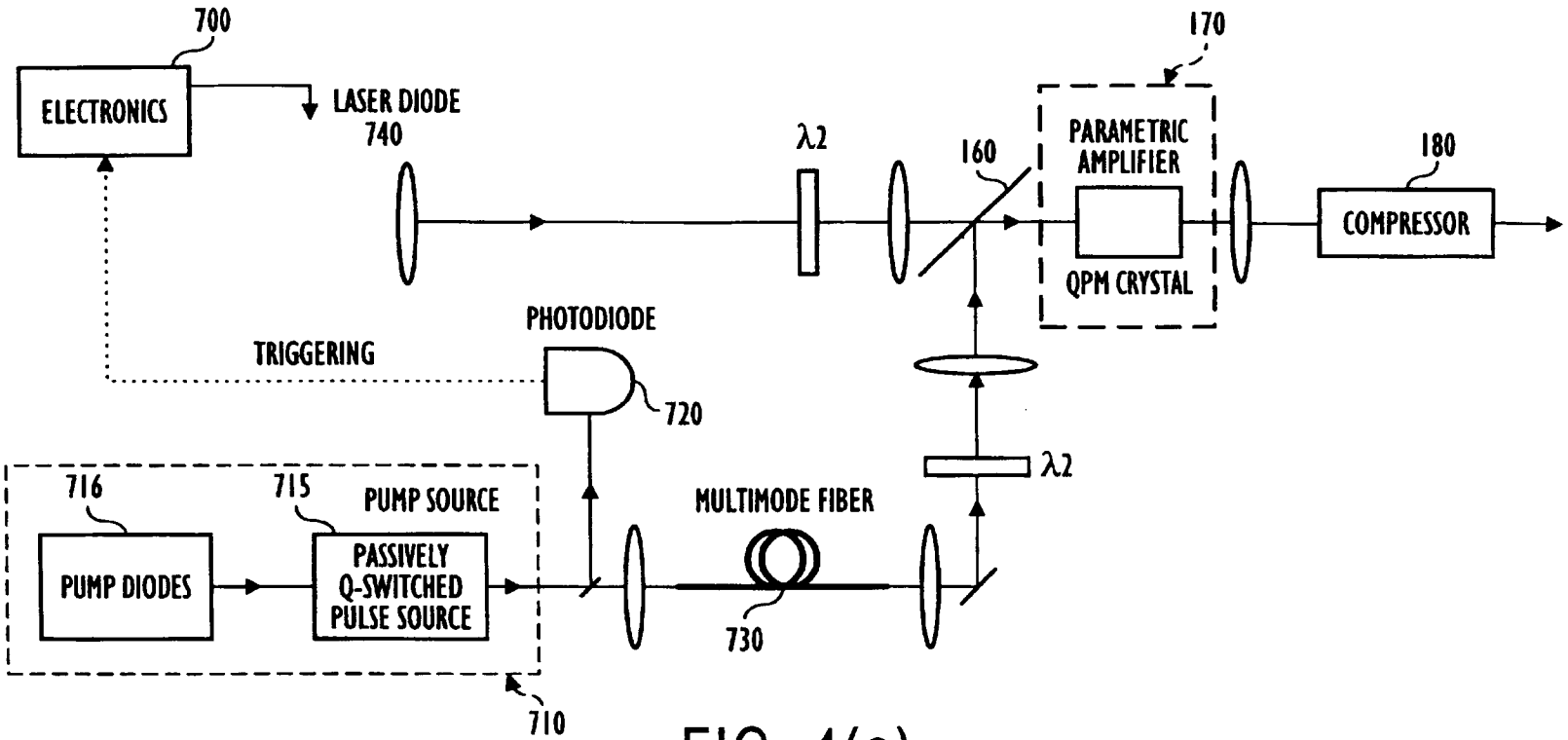
FIG. 4(a) and 4(b) depict passively and actively Q-switched solid state laser based systems according to a second embodiment of the present invention.
Figure 4B:
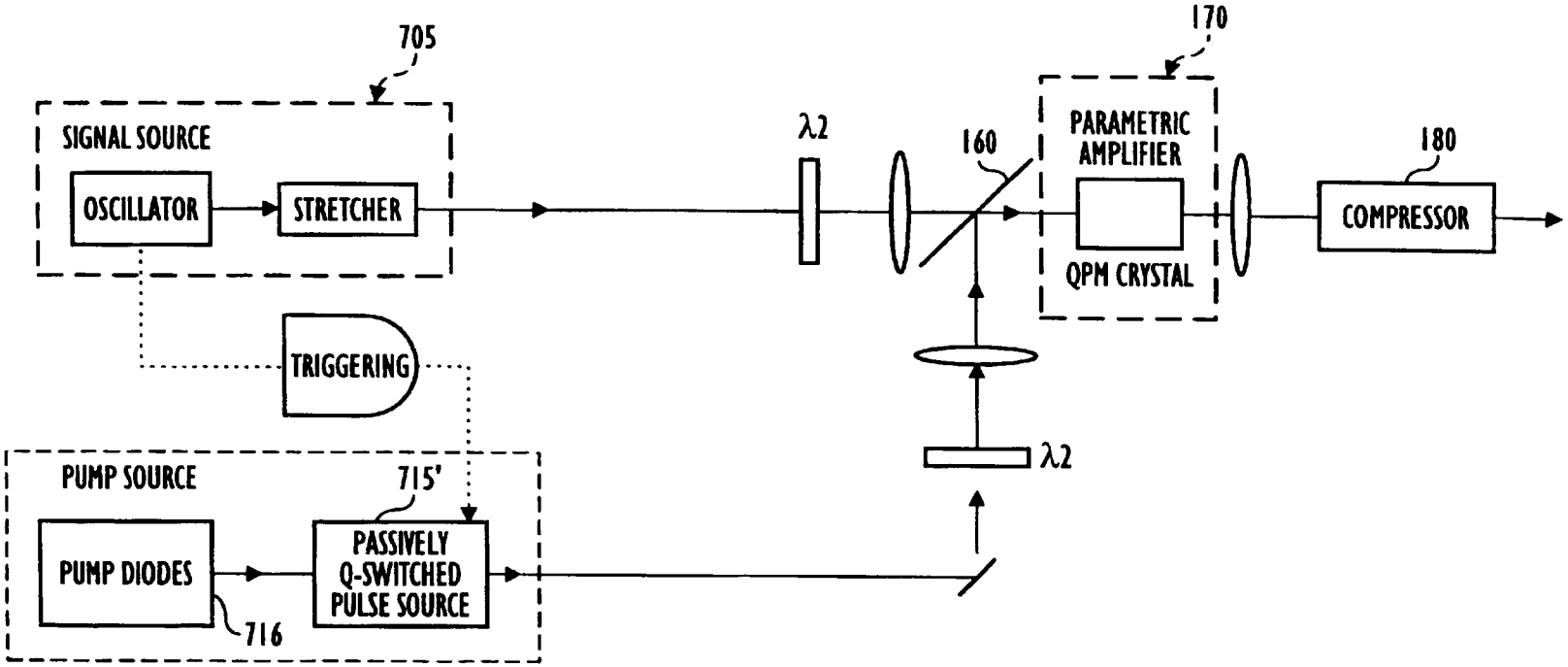

According to another exemplary embodiment shown in FIGS. 4(a) and 4(b), the present invention is implemented using a Q-switched solid-state laser system.

Several solid state materials can be laser diode pumped, which makes it possible to design compact and robust solid-state based sources for pumping a stretched-pulse parametric amplifier.

Q-switching is the well established technique which allows generation of high peak power pulses. The Q-parameter of an optical cavity is defined as the ratio of energy stored in the cavity to that lost per round trip. It can be varied by varying losses in the cavity. There are two methods to control losses: active Q-switching and passive Q-switching. Active Q-switching requires some active modulator in the cavity (e.g., a Pockels cell). The advantage of actively Q-switched lasers is that they can be triggered externally. Passive Q-switching can be implemented using a passive device, such as a saturable absorber. An essential drawback of passively Q-switched lasers is that their triggering is not controlled externally and pulse-to-pulse jitter has a large magnitude, which can exceed the duration of the pulse itself. This feature makes synchronization between a mode-locked and a passively Q-switched lasers a serious problem. However, the inventors have found that this problem can be avoided and the energy of passively Q-switched lasers can be utilized for a parametric amplification scheme, provided that an externally synchronizable laser, such as, e.g., a fast-tuned laser diode, is used as a source of stretched broad-bandwidth pulses. Such a laser diode can be easily triggered by either a passively or actively Q-switched laser with negligible timing jitter. In general, any externally synchronizable laser (e.g., a gain switched laser diode) can be used instead of the fast tuned diode.

An example of such an embodiment using a Q-switched solid state laser is shown in FIG. 4 (a). The pump source 710 comprises a passively Q-switched pulse source 715 which is pumped by pump diodes 716. Tunable diode electronics 700 which control the tunable laser diode 740 are triggered by a small fraction of the optical output of the Q-switched pulse source 715 (for high energy pulses about 1% is sufficient), which is detected with a fast photodiode 720.

In cases where it is necessary to compensate for the unacceptably large delay of the diode driving electronics, the pump pulse can be launched into a delay line, here implemented in multimode fiber 730. The size of the core of the fiber has to be sufficiently large to avoid nonlinear distortions and to achieve good in-fiber coupling efficiency. Use of this fiber facilitates the implementation of the present embodiment, but is not essential.

Implementation of an actively Q-switched pump source is shown in FIG. 4(b). Such pump source 715' can be triggered externally with negligible jitter, thus allowing use of a mode-locked signal source 705.

In both FIGS. 4(a) and 4(b), to increase pump pulse energy, Q-switched pulses can be further amplified in a solid-state amplifier (not shown).

A particularly attractive concept for manufacturing compact Q-switched solid-state lasers is the microchip laser, which involves the use of semiconductor packaging technology. Thousands of microchip lasers can be fabricated from a wafer of a solid-state laser material, by polishing so that the two surfaces are flat and parallel, subsequently coating these surfaces with dielectric mirrors, and by dicing the wafer using standard semiconductor dicing techniques. Such "chip lasers", which are approximately 1-3 $mm^3$ in size, can be pumped with single-mode or multi-mode laser diodes or diode arrays. Typical materials for microchip lasers are Nd-doped such as YAG, with operating wavelengths at 1064 and 1319 nm and laser-diode pumping at about 808 nm. Q-switching has been accomplished by bonding either an electro-optic (active device) or saturable absorber medium (passive device) to Nd:YAG or Nd:$VO_4$ microchips to form a composite cavity. The Q-switched output of a single microchip laser can be up to several tens of microjoules with durations from hundreds of picoseconds to nanoseconds, e.g., 200 ps to 5 ns. Use of microchip lasers allows very cheap and compact microjoule femtosecond pulse sources. Furthermore, by using microchip laser arrays, power and energy scaling can be achieved and output energies of up to about 100 mJ are possible.

The use of a QPM parametric crystal according to the present invention allows use of compact sources, such as microchip lasers, which produce relatively low output energies, as pumps for a PCPA system. In contrast, using conventional nonlinear materials (such as BBO), even the tight focusing of the pump beam cannot provide sufficient parametric gain for efficient power conversion.

Figure 4C:
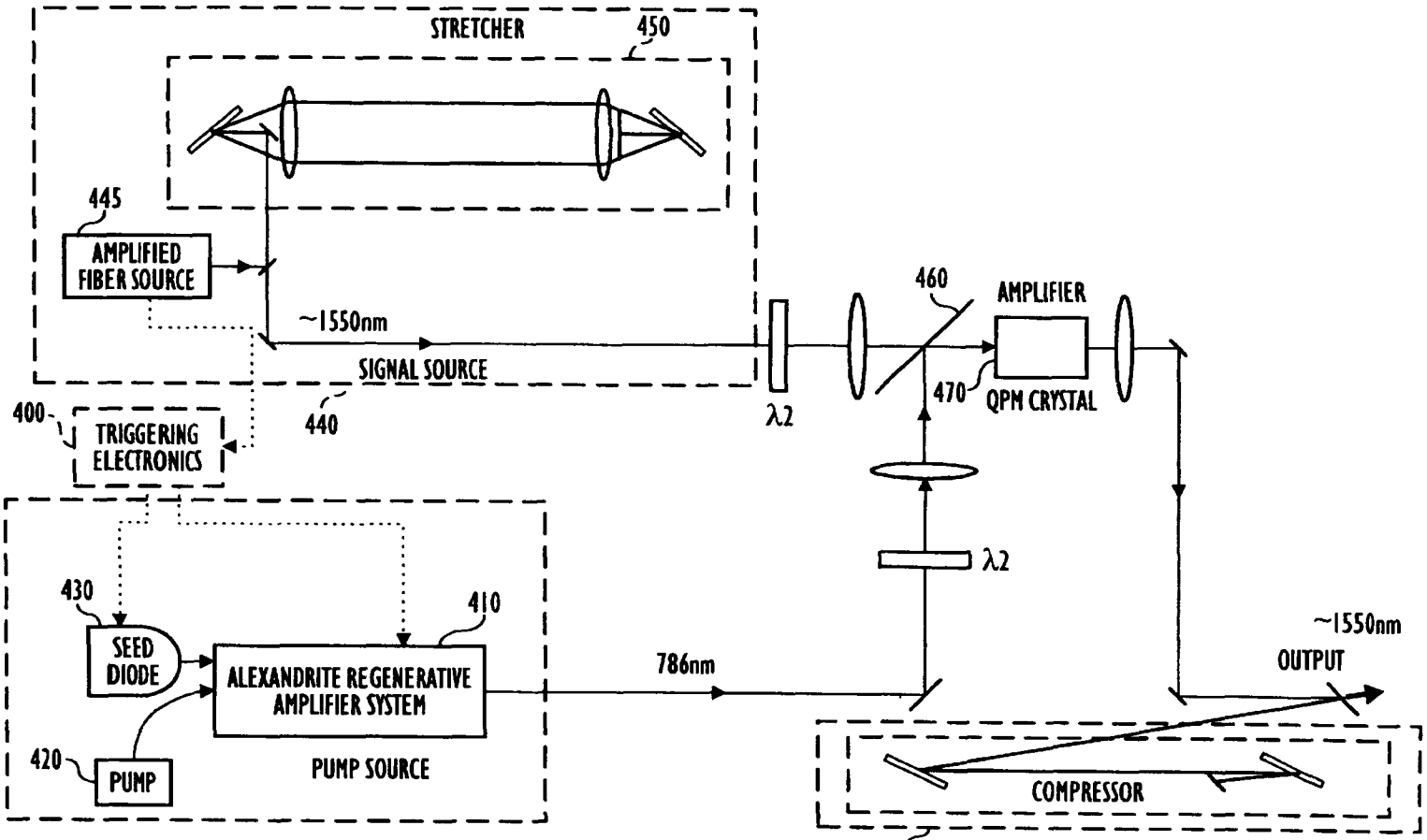
FIG. 4 (c) depicts a MOPA-type alexandrite-based system according to a further embodiment of the present invention.
FIG. 4(d) depicts the alexandrite regenerative amplifier arrangement according to the further embodiment of the present invention.
Figure 4D:
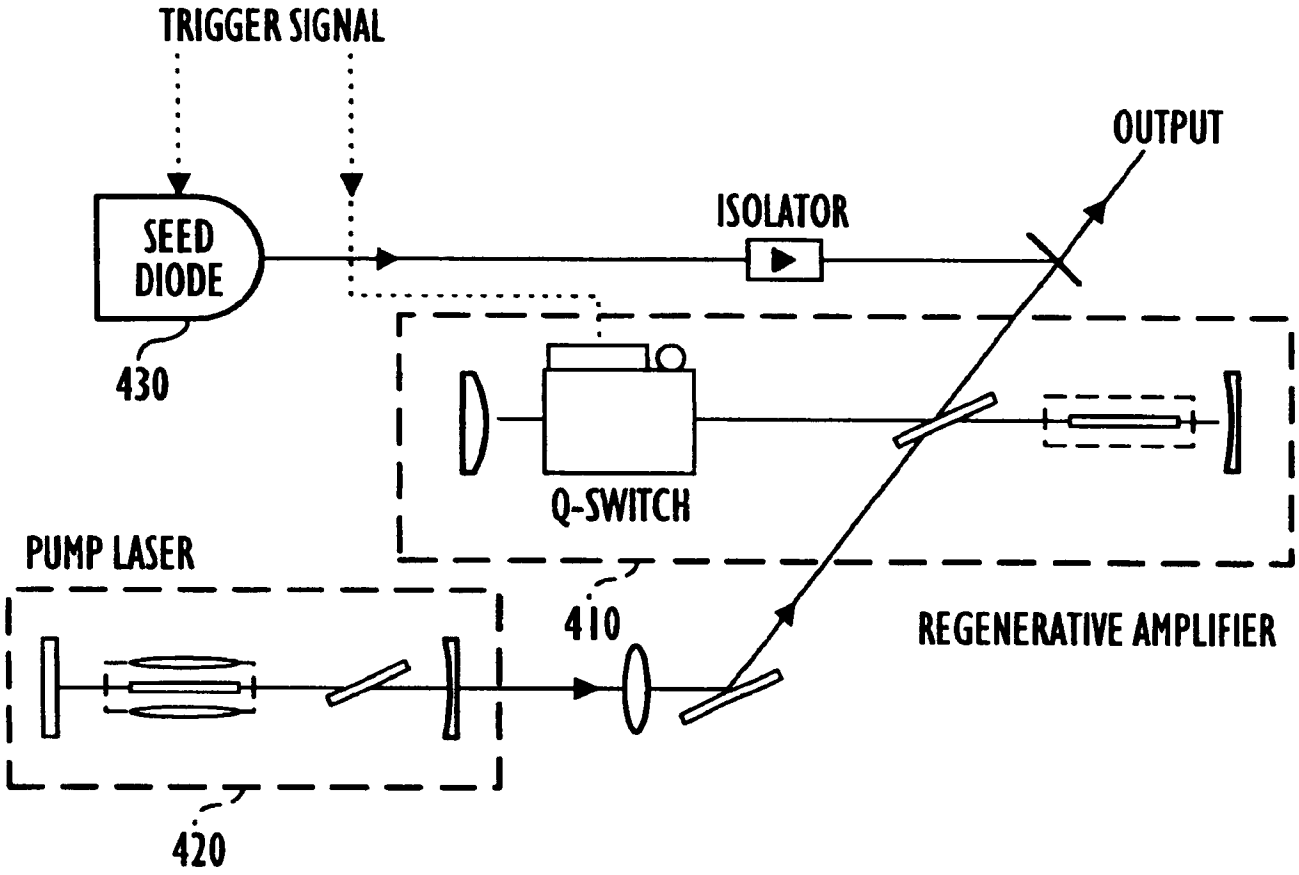
Figure 5A:
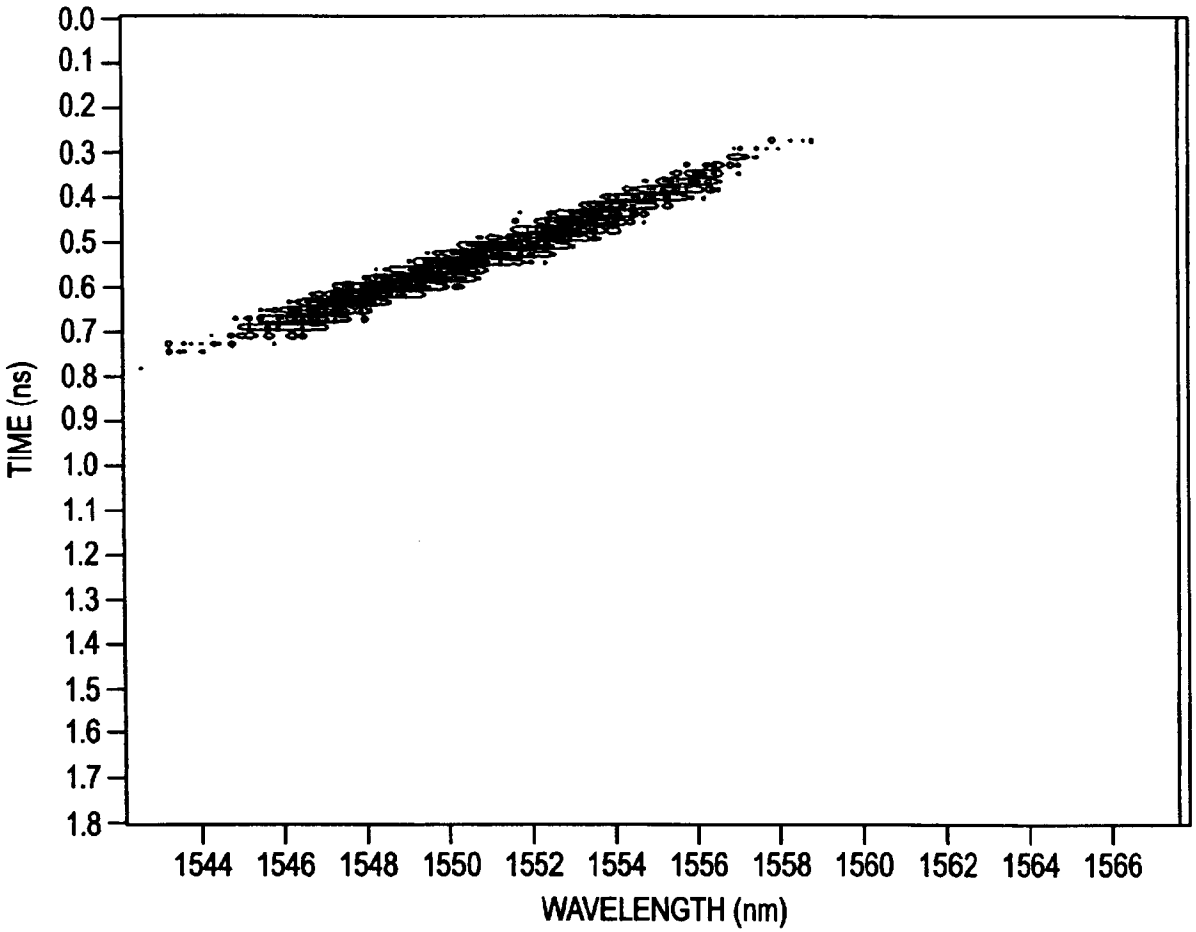
FIG. 5(a) is a streak image of the unamplified signal beam produced by the system of the embodiment of FIG. 4(c).
Figure 5B:
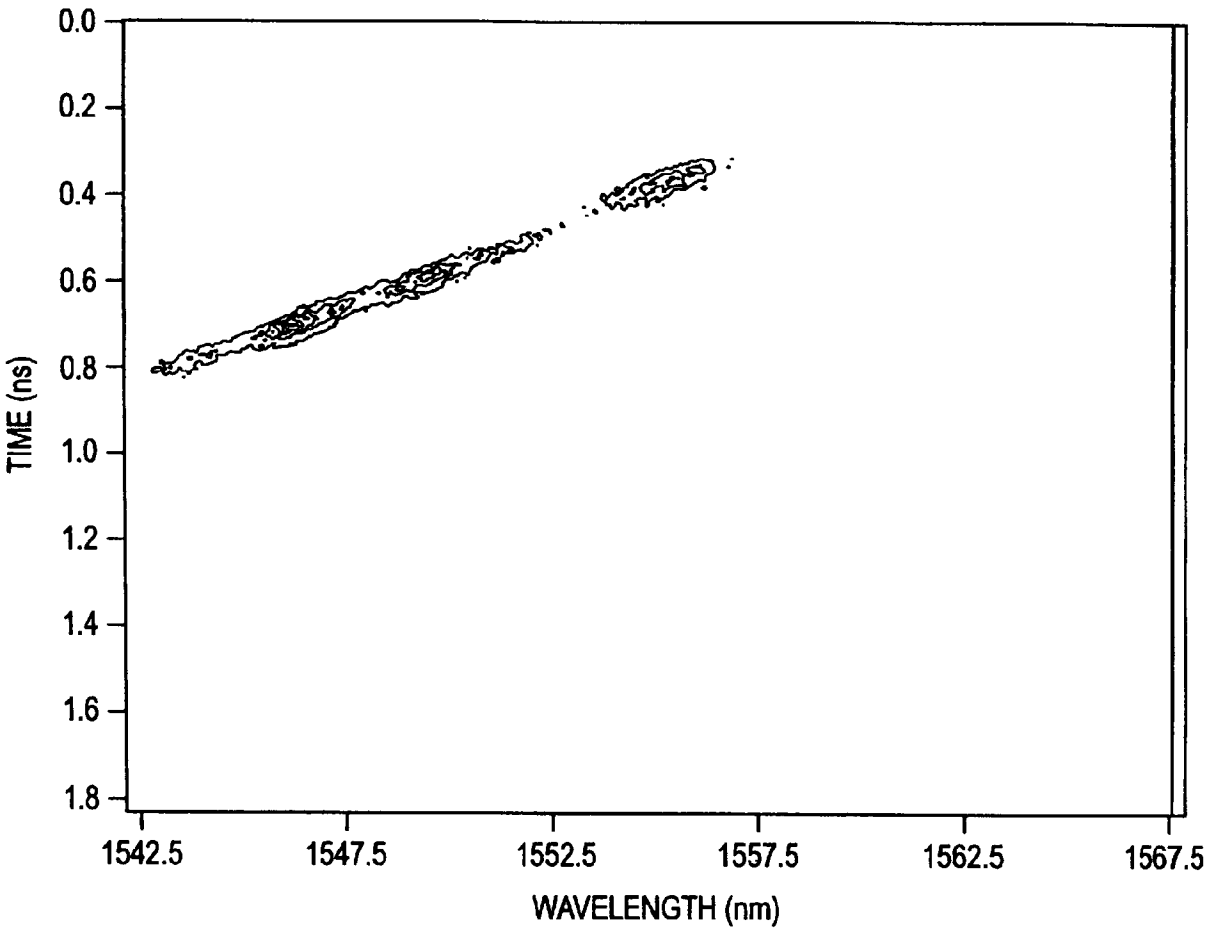
FIG. 5(b) is a streak image of the amplified signal beam produced by the system of this embodiment.
Figure 5C:
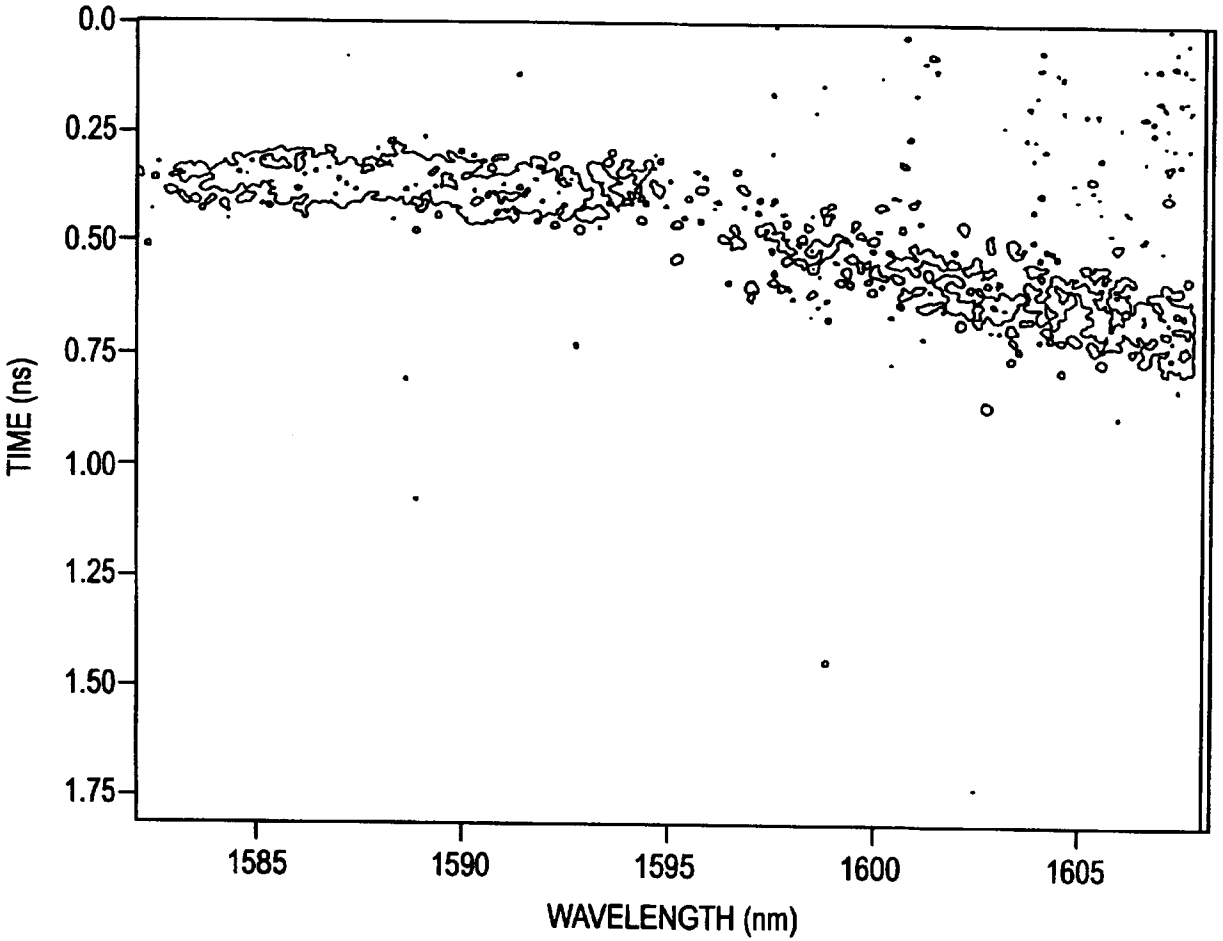
FIG. 5(c) is a streak image of the idler phase of the system of this embodiment.
Figure 5D:
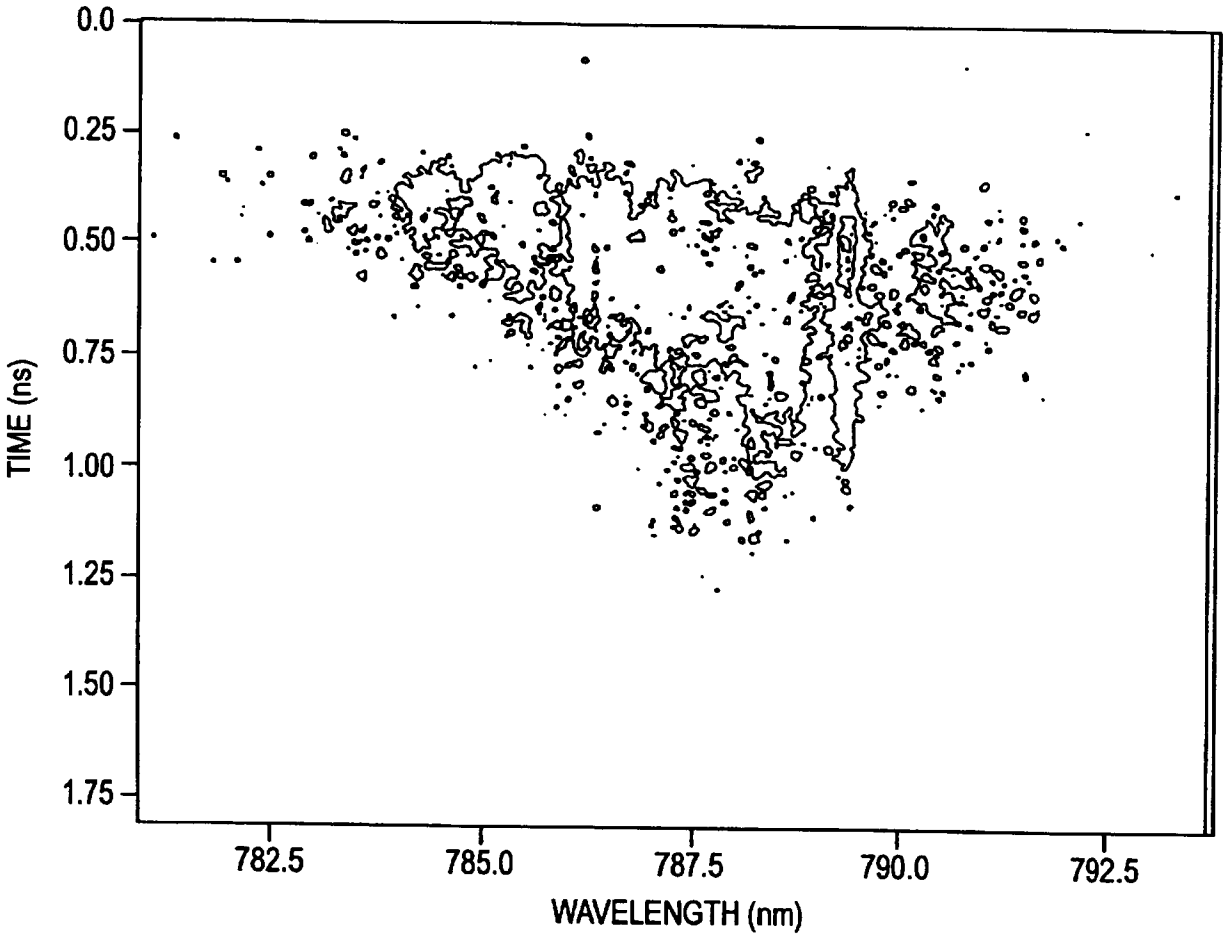
FIG. 5(d) is a streak image of the pump signal of the system of this embodiment.
Figure 6:
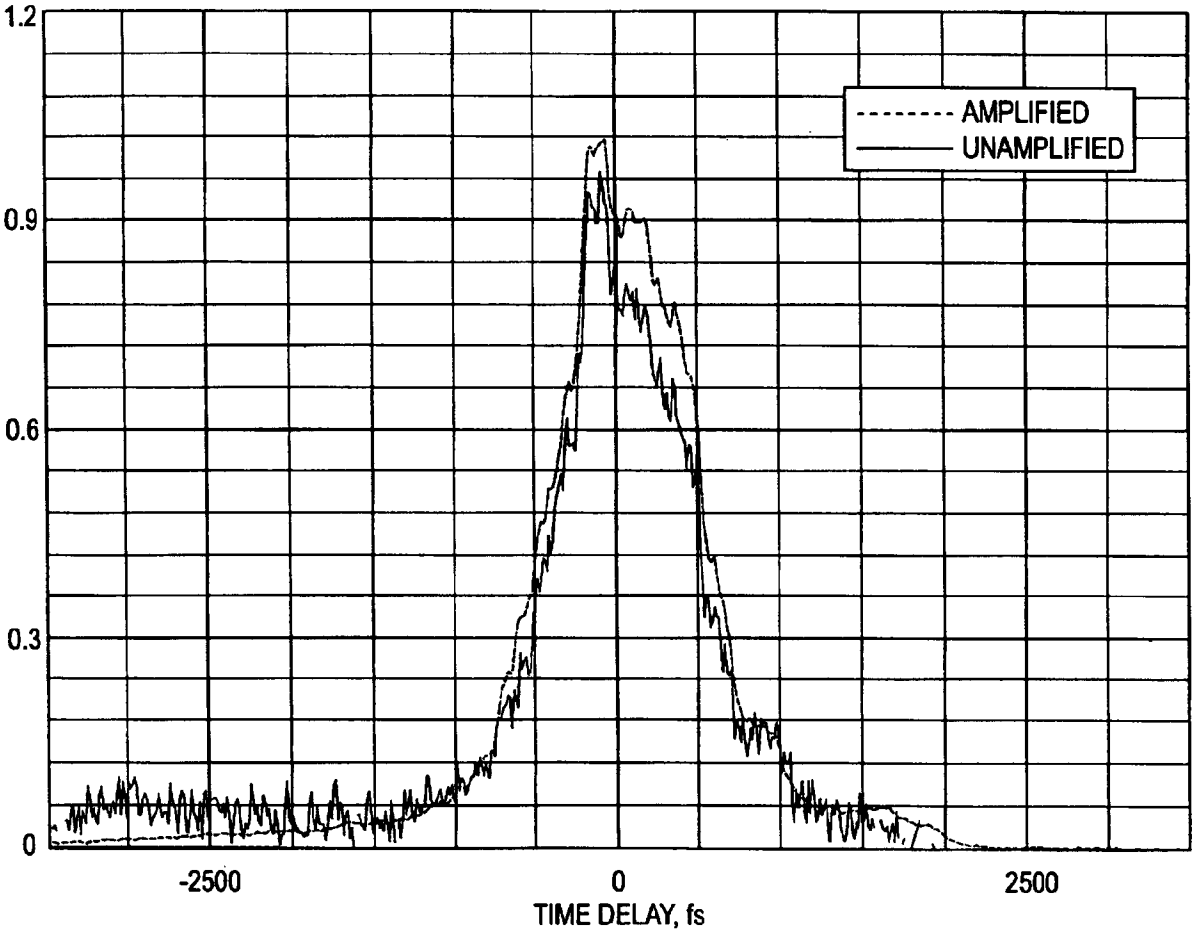
FIG. 6 is a plot of the single-shot autocorrelations of the amplified and unamplified pulses of the system of the embodiment of FIG. 4 (c).

According to a further exemplary embodiment shown in FIGS. 4(c) and 4(d), the present invention is implemented as a solid-state based PCPA system.

As explained above, in the prior art using conventional birefringent phase-matched BBO crystal in a noncollinear configuration, 1:30 energy conversion efficiency has been achieved with 3 mJ and about 5 ps pump pulses. However, in order to utilize nanosecond pump pulses with the same required peak powers, the pump energies would have to be increased 100 to 1000 times. This would necessitate employing pulse sources with output energies at the Joule level. At present, as is known to those skilled in the art, such systems are large, cumbersome and expensive. Also, the pulse energy densities of such sources are typically above the damage threshold of the non-linear media. The use of QPM materials according to the invention reduces the requirement on the pump energies down to the microjoule and millijoule levels, and attendantly reduces the power densities to levels below the damage threshold of the nonlinear crystal. At this energy level, there are a variety of practical solid-state systems which can provide the required pump pulses for a PCPA system.

MOPA schemes, essentially similar to those as described above using a fiber amplifier, can be also implemented with bulk solid-state materials. However, due to the low single-pass gain of a solid-state medium, multipass or regenerative schemes are preferable.

The general arrangement of a MOPA-type alexandrite-based system is shown in FIG. 4(c). A lamp pumped multimode alexandrite laser is used as a pump laser 420 for an alexandrite regenerative amplifier 410 operating at wavelengths between 780 nm and 800 nm (FIG. 4(d)). The amplifier is seeded with variable-duration pulses from a standard semiconductor laser seed diode 420 at 786 nm. The duration of the diode pulses is determined by the electric pulse duration from a standard nanosecond pulse generator of triggering electronics 400. The repetition rate of the alexandrite system is 10 Hz. It was found that the amplified output provides 350 ps-1 ns pulses (as determined by the seed duration) with energies as high as 8 mJ. The cavity is switched out after a fixed number of round trips. This, along with the fact that the seed-diode is externally triggered, greatly facilitates timing of the pump pulse with the signal pulse.

The signal source 440 is an amplified Er-doped fiber laser system operating at about 1550 nm wavelength. Femtosecond pulses from a passively modelocked Er-doped fiber laser source 445 are stretched in a positive-dispersion diffraction-grating stretcher 450 and amplified in a chain of diode-pumped Er-doped fiber amplifiers (not shown). After amplifications, pulses of about 7 nm bandwidth (determined by the gain narrowing) and 300-350 ps long were obtained. This system can provide seed pulses with energies of up to 10 μJ. Such high energies were used for convenience, in order to work with a single-stage parametric amplifier. Amplification of the direct output from the oscillator and the pulse stretcher would generally require two parametric-amplification stages in order to reach millijoule energies. Compared to quantum amplifiers, parametric amplifiers can be seeded with substantially lower energies. This is because the injected low-energy pulses in a parametric crystal have to compete with vacuum fluctuations, as opposed to the spontaneous emission of a quantum amplifier.

The pump and signal pulses are combined in an IR beam-splitter 460 for collinear propagation. Both beams are focused into a sample of periodically poled lithium niobate (PPLN) QPM crystal 470. The thickness of the crystal was 0.5 mm and a variety of lengths from 3 to 5 mm were employed. Even longer crystals can be used, which would further decrease the required pump energies and alleviate crystal damage problems. The quasi-phase-matching period of the PPLN crystal in this particular implementation was 19.75 μm. In general, the QPM period A can be calculated for a given interaction by using the following equation:

$$\frac{1}{\Lambda} = \frac{n_p}{\lambda_p} - \frac{n_s}{\lambda_s} - \frac{n_i}{\lambda_i},$$

Here, $n_k$ and $\lambda_k$ are the refractive indices and wavelengths at the pump, signal and idler wavelengths respectively. It is obvious from this equation that the pump wavelength can be selected by choosing the proper quasi-phase-matching period for the parametric amplifier. It is also clear from this equation that if the QPM period is chirped along the optical beam path, it in effect broadens the phase matching bandwidth for a given nonlinear interaction. The chosen geometry of the crystal provides noncritical phase matching, thus eliminating beam spatial walk-off. Optimum conversion efficiency from pump to signal is critically dependent on spatial overlap and collinearity of the pump and seed beams in the crystal. The pump and signal spot-size diameters can be, for example, in the range of 300 to 400 μm. Large spot diameters at the crystal are essential for both preventing crystal damage and for spatial matching of multiple-mode and single-mode profiles of pump and signal beams. No special care need be taken to match the wavefront curvatures of the pump and the signal beams in the crystal. The amplified pulses are recompressed with a standard negative-dispersion diffraction-grating compressor 480.

A maximum amplified signal output of 1 mJ was experimentally obtained with mJ of pump and 100 nJ of signal inputs. A small-signal gain of $10^4$ was measured for input pulse energies of 5 nJ and less. Pump-to-signal conversion efficiency was found to be as high as 35%. Although the pump beam in this system is single-mode, pumping conditions are equivalent to the pumping with a multimode beam due to the mismatch between the wavefront curvatures and due to large sizes of both beams in the parametric crystal. For large spot sizes and high mode numbers, the spatial mismatch between single-mode and multimode beam profiles is negligible.

The material properties of lithium niobate allow efficient parametric conversion at pump intensities below the crystal damage threshold. For 300 ps-500 ps pump pulse durations, as used for the amplification, no damage was observed even with the maximum pump energies of 8 mJ. However, for pump pulsewidths of longer than 1 ns, optical damage of the entrance facet of the parametric crystal was observed at about 2 mJ/pulse, corresponding to an intensity of 3.8 GW/cm$^2$. At longer pulsewidths, i.e., 5 ns, surface damage was observed at even lower peak intensities of 0.8 GW/cm$^2$, which could produce only negligible parametric gain. The observed dependence of the damage threshold on the duration of the pump pulses is consistent with the surface-damage of bulk $LiNbO_3$ due to the thermal effects. This indicates that pumping with shorter than 1 ns pulses is advantageous for $LiNbO_3$ crystals for obtaining the highest parametric gain and conversion efficiency.

In general, for a given pulse duration the useable pump energies (and consequently the obtainable signal energies) can be scaled up or down by adjusting the spot area proportionally. This preserves the fixed pump intensity. The only practical limitation on the obtainable maximum energies is set by the maximum transverse dimensions of the parametric crystal. Currently, 0.5 mm thickness periodically poled lithium niobate is the standard, as determined by limitations on electric field poling. Spot size scaling beyond this limit would require asymmetric beam expansion to utilize the unrestricted width of the crystal. However, the thickness of the QPM crytal can be increased to a required or desired size, i.e., by using a diffusion-bonded vertical stack of PPLN plates.

Figure 7:
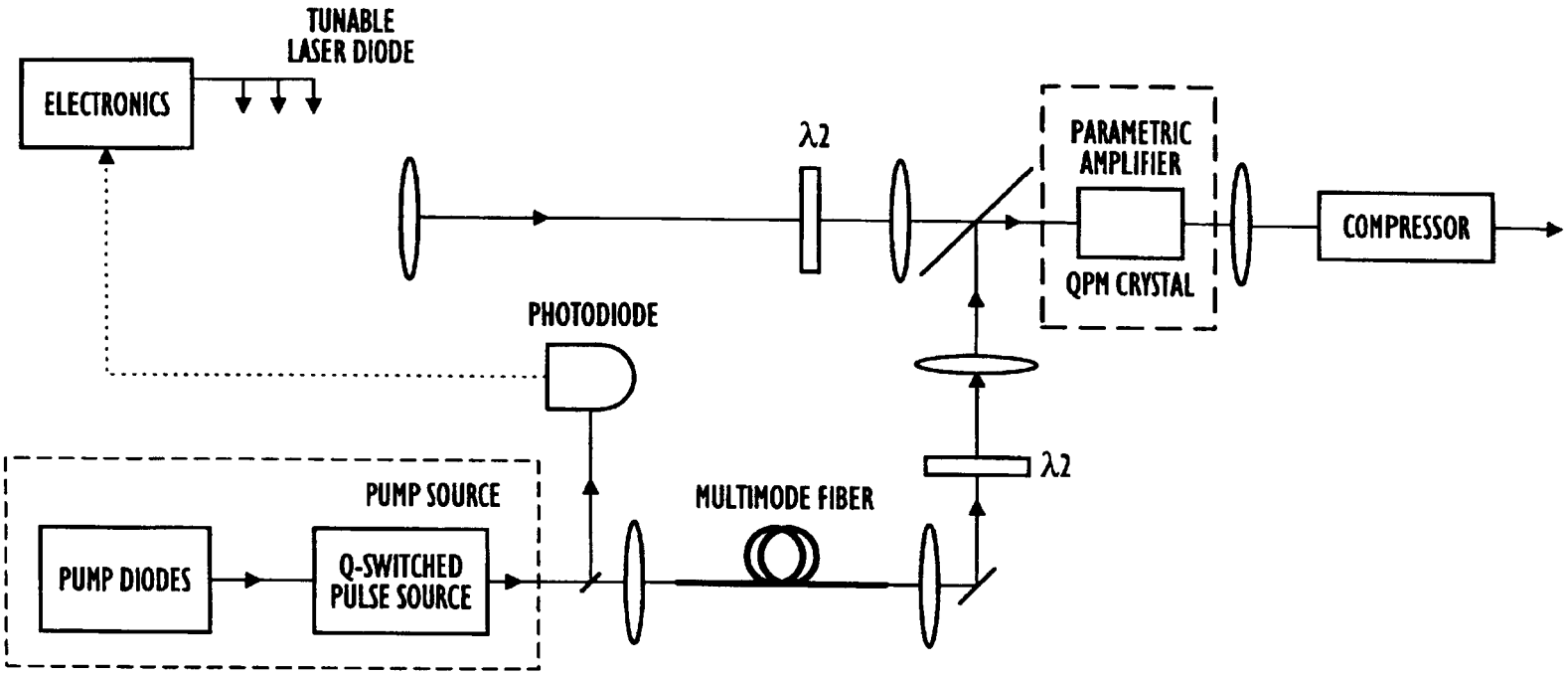
FIG. 7 illustrates a further embodiment including a novel pump source.

It is important to verify that parametric interaction between the pump and the signal does not induce phase distortions on the amplified stretched pulse. In order to characterize the chirp on the amplified output, the recollimated output was spectrally dispersed in a grating mono-chromator and A further embodiment is shown in FIG. 7, which is a variation of the system previously described in connection with FIG. 2. The embodiment of FIG. 2 used a diode laser as a seed and large-core multimode fiber amplifiers for obtaining millijoule and higher pulse energies. This fiber amplifier could be implemented preferably with an Er-doped fiber amplifier operating in the 1530-1560 nm wavelength range. Plural amplification stages with optical gates in between and subsequent second-harmonic generators were required.

FIG. 7 illustrates a related approach, which is much simpler and significantly more efficient. A diode-pumped microchip laser 72 is used as a seed source, operating at~1064 nm and producing~1 ns pulses with energies of 1-10 μJ and at repetition rates of 1-10 kHz. These pulses are injected into Yb-doped large-core (10-100 μm diameter) cladding pumped fiber amplifier 74 such that millijoule pulses with a few watts of average power can be produced. Due to the high energy of the seed pulses (microjoules as compared to picojoules from a diode laser) and the large gain of an Yb-doped fiber, no multiple stages or optical gates are required to obtain millijoule pulses and a few watts of average power. Further, no second-harmonic is required to parametrically amplify femtosecond pulses from a mode-locked Er-fiber laser at a~1550 nm wavelength. Frequency doubling of 1064 nm pulses allows 532 nm pulses to be obtained which are suitable for pumping parametrically an~800 nm output from Ti:sapphire femtosecond modelocked oscillators, if desired. The Yb-fiber amplifier has considerably higher quantum efficiencies compared to Er-fiber (60-80% for Yb as compared to 20-45% for Er) and to any solid-state amplifier. The efficiency of the diode-pumped Yb-fiber system can be much higher than of any other diode-pumped nanosecond laser, reducing overall cost and complexity of the PCPA system.

Active-ion concentration in the Yb-fiber can be much higher than in Er-fiber. This leads to significantly shorter amplifier lengths and, consequently, to significantly less susceptibility to nonlinear scattering effects in the fiber core. Yb-fiber has significantly higher saturation fluence compared to Er-fiber, facilitating extraction of higher pulse energies. Due to this high saturation fluence, Yb-doped solid state amplifiers are also advantageous compared to other solid-state gain media in extracting very high pulse energies (up to several joules).

Figure 8:
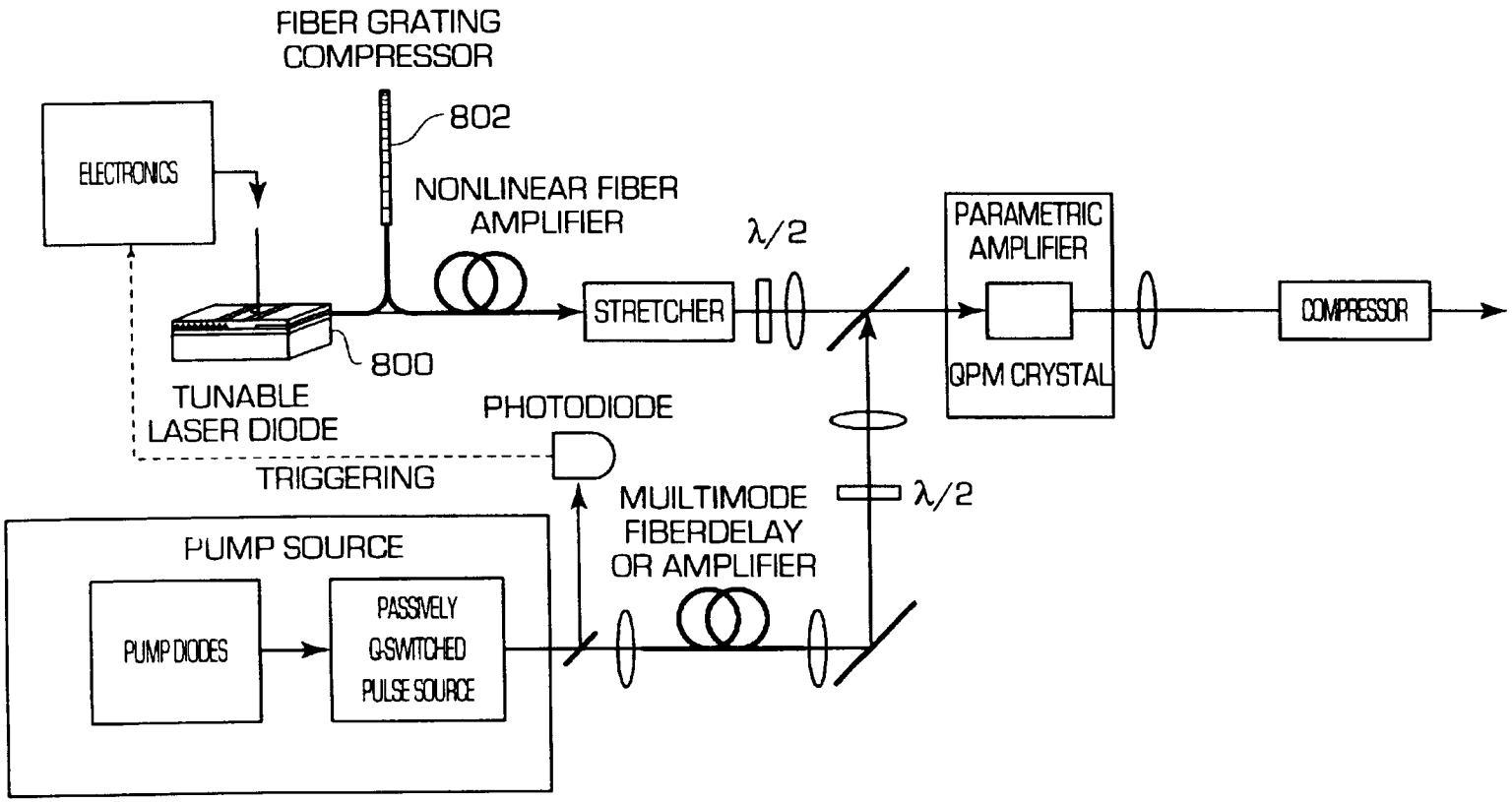
FIG. 8 illustrates a further embodiment of a diode-based source.

A still further embodiment is illustrated in FIG. 8, which is a variation of the embodiment of FIG. 4(a). In FIG. 4(a), a semiconductor tunable laser generates ultrashort pulses which are externally triggered. This allows use of passively Q-switched lasers. An advantage of this arrangement is the attainment of order-of-magnitude higher pulse energies and powers directly from a diode pumped and passively Q-switched microchip laser for pumping PCPA. Another advantage stems from the simplicity of passively Q-switched lasers compared to actively Q-switched lasers.

FIG. 8 illustrates a similar approach where the output from a tunable laser or gain switched diode laser 800 is compressed in a fiber grating 802 to a few picosecond duration (typically 1-3 ps) and subsequently launched into a standard single-mode rare-earth fiber amplifier (an Er-doped fiber amplifier, for example). Nonlinear effects (soliton formation) can be advantageously used here to generate nonlinearly-compressed femtosecond pulses. Equivalently, stretched pulses can be amplified first and then compressed in a fiber grating and then launched into additional fiber for nonlinear pulse shortening. Standard gain-switched diodes can be used to produce 10-300 picosecond pulses directly, which can be subsequently compressed in a nonlinear fiber amplifier.

PCPA systems of the types described above will make it possible to replace many of the competing ultrafast laser systems with shoebox-size millijoule systems in a variety of applications. In the following, several application systems 181 are described in combination with the inventive laser system. While only these several applications are described in detail, it will be understood by those of skill in the art that the PCPA system of the invention can be used generally in replacement of amplified ultrafast Ti:sapphire laser systems, and also in replacement of other current laser systems in many cases.

Low-power machining and micromachining

Application system 181 may typically be an industrial laser system of known construction. Such systems are used for material cutting and drilling and currently predominately employ $CO_2$ or Nd:YAG lasers. Most laser micromachining is typically done with Nd:YAG, eximer, or copper-vapor lasers. PCPA ultrafast lasers have important advantages over these other lasers for higher-precision work. When femtosecond pulses are used to drill or blast away material, the surface layers of the material are vaporized instantly without depositing heat in the material. When using ns and ps laser pulses, much of the material surrounding the target point is melted and resolidified. This surrounding area—called the heat affected zone (HAZ)—can be very ragged and rough. However, according to the combination of the invention, when ultrashort laser pulses (USLP) are used, no melt is produced, making the cuts much cleaner and better controlled. Use of USLP also minimizes the size of the shock affected zone (SAZ), which is surrounding area of material fractured by the powerful ultrasonic shock wave produced by the rapid heating effect of ns and ps laser pulses. The minimization of the SAZ results in cleaner cuts, and less collateral damage to the areas around and underneath the cut when using fs pulses.

Femtosecond lasers also have additional advantages for machining. The physical mechanism for ablation with fs pulses is more deterministic and controllable than for ns pulses. Because of this, it is possible to machine features which are smaller than the laser spot size. For example, using an ultrafast laser, it is possible e.g., to drill 0.3 micron diameter holes in a silver film using a beam spot size of 3.0 microns. This capability indicates that ultrafast lasers can replace excimer lasers in some micromachining applictions. Currently, excimer lasers are used for high-precision machining due to their short wavelength (~200-300 nm). But excimer lasers are expensive and troublesome and require equipment for handling of corrosive and toxic gases. The solid-state alternative to excimers provided by the invention is thus of great benefit to this industry.

Femtosecond laser machining has been demonstrated with many materials, such as stainless steel and other alloys, plastic, tooth enamel, glass, diamond, and many others. The required laser pulse energy for cutting usually depends greatly upon the material properties, especially its optical absorption. For example, it is more difficult to cut transparent materials because they do not absorb much light. Femtosecond laser pulses, however, exhibit less sensitivity of the ablation threshold to material absorption, so that even transparent materials can be cut or drilled quite easily.

As one specific example, using ultrafast lasers for drilling results in better reproducibility in the micromachining of biosensors (for glucose monitoring).

Laser Surgery, Drilling, And Cutting

Application unit 181 may alternatively be a surgical knife or other tool. Ultrashort laser pulses provide great advantages in the cutting and drilling of biological materials and tissue. As with non-biological materials, ultrashort laser pulses can ablate tissue (either hard or soft) with very little local heating or collateral damage to adjacent areas as compared with microsecond or nanosecond lasers. The cuts are more precise, and there is less damage to the surrounding tissue. This promises a new level of high precision in medical laser treatment. One example is in ocular surgery. Conventional pulsed lasers cannot be used in a number of procedures due to the severe collateral damage which is generated in the shock affected zone. Femtosecond lasers by contrast have been used to demonstrate high precision refractive surgery. The laser is used to cut a small flap in the cornea to make way for subsequent procedures. The flap cut with the femtosecond laser is quite smooth in comparison with the flap cut by the knife in a device called a microkeratome, which is currently used clinically.

When application unit 181 is a medical instument or surgical tool used to drill or remove hard tissue (such as a dental drill, as one example, using the PCPA based USLP of the invention has the following advantages over nanosecond laser pulses:

- lower energy thresholds for efficient material removal (3 $J/cm^2$ using USLP vs. 20-35 $J/cm^2$ using ns pulses)
- ablation threshold is much less sensitive to tissue type
- cleaner holes with less collateral damage
- smaller temperature rise in tissue. For example, in teeth, 2° C. for USLP versus >50° C. rise using ns pulses)
- lower noise levels (much less than a dental drill)

Industrial Laser Applications

In many industrial processes, lasers have a number of advantages over more traditional mechanical methods such as drilling, machining, cutting, surface treatment, paint stripping, etc. One of the better known advantages is related to the very high precision which can be obtained with lasers.

One of the lesser known advantages of using lasers is the reduction of solid and liquid waste in many applications. In one example, where application unit 181 is a paint removal application system, the amount of waste can be reduced by more than 50 times as compared with traditional chemical methods.

Materials processing, including cutting, marking, drilling, scribing, welding, soldering, sintering, surface treatment (including hardening and alloying), lithography, and can be performed using the lasers according to the invention when the application unit 181 is a suitable machine tool. A number of arts use these processes, such as semiconductor and microelectronic processing as well as rapid prototyping, desktop manufacturing, and micromachining.

Commercial electronics application units according to the invention include include precision micromachining and thin-film trimming systems. The trimming applications include the well-established memory repair, as well as trimming the sensor for air bags and gold coatings on quartz watches. Newer applications that have been receiving much interest include rapid prototyping for model building.

In some materials, there appears to be a large advantage to using fs lasers for high-precision work. Among the materials which show real improvement when drilled or machined with femtosecond lasers are silicon, steel, copper, gold, some polymers, hard dental tissue, and soft ocular tissue (corneal).

This may be explained to a degree by experiments which show that the pulsewidth dependence of LIB indicate that the damage fluence threshold decreases with pulsewidth (as $^{1/2}$) down to a pulsewidth of 10 ps. Then it increases slightly as the pulses become even shorter. This holds true for $SiO_2$ and for $MgF_2$ in particular.

In the low-fluence regime, femtosecond pulses yield much better surfaces than nanosecond pulses. For example, when the application unit 181 is a femtomachining system, very smooth surfaces are obtainable with some materials. For example, after ablating a silicon surface with threshold pulses of (0.13 J/cm$^2$, 80 fs) an AFM image exhibits a surface roughness of approximately 30 nm.

Intergrating fs Lasers Into Large Industrial Systems

The concept here is to inject 10 micron pulses from a PCPA system into a large, high-power $CO_2$ laser oscillator either to injection modelock the $CO_2$ laser (for high average powers~1 kW) or for regenerative amplification to high pulse energies (~20 J). Experiments have shown the potential of using $CO_2$ lasers for high-average power production of short pulses, but the systems were not practical. The reason is that the injected pulses were obtained by plasma-shuttering a CW $CO_2$ laser, using pulses from a picosecond amplified dye laser system as the activating pulse for the plasma-shuttering. Using a PCPA system as the injector for a $CO_2$ laser makes such system practical. A system using a $CO_2$ laser as the final stage is very attractive from the standpoint of power efficiency, since $CO_2$ lasers are power efficient.

Although the invention has been described and shown in terms of preferred embodiments thereof, it will be understood by those skilled in the art that changes in form and detail may be made therein without departing from the spirit and scope of the invention as defined in the appended claims.

What is claimed is:

1. An optical pulse amplification and delivery system, comprising:

a pump source generating optical pump pulses of a predetermined duration;

a signal source generating optical signal pulses;

combining elements receiving and combining the optical pump pulses and the optical signal pulses, and providing combined optical pulses which are substantially temporally overlapped; a parametric amplifier comprising a quasi-phase-matched crystal receiving the combined optical pulses and amplifying the optical signal pulses using energy of the optical pump pulses;

a compressor which compresses the amplified optical signal pulses to a time duration substantially shorter than the predetermined duration of said optical pump pulses; and an application unit receiving an output of said compressor and applying said output to a specified location.

2. A system as claimed in claim 1, wherein said application unit comprises a machine tool.

3. A system as claimed in claim 1, wherein said application unit comprises a surgical instrument.

4. A system as claimed in claim 1, wherein said combined optical pulses as delivered to said application unit, are femtosecond regime duration pulses.

5. A system as claimed in claim 1, wherein said pump source comprises one of a diode laser system and a diode laser system combined in cascade with a Yb fiber amplifier system.

6. The optical pulse amplification system of claim 1, wherein said signal source comprises:

a signal pulse generator; and a stretcher receiving and stretching signal pulses generated by the signal pulse generator, to a duration approximating said predetermined duration.

7. The optical pulse amplification system of claim 1, wherein said predetermined duration is greater than about 100 picoseconds.

8. The optical pulse amplification system of claim 1, wherein said pump source is a multimode source.

9. The optical pulse amplification system of claim 1, wherein said pump source comprises at least one multimode fiber amplifier.

*10. An optical pulse amplification and delivery system, comprising:*

*a pump source generating optical pump pulses;*

*a signal source generating optical signal pulses;*

*combining elements receiving and combining the optical pump pulses and the optical signal pulses, and providing combined optical pulses which are substantially temporally overlapped;*

*an amplifier including a non-linear crystal receiving the combined optical pulses and amplifying the optical signal pulses using energy of the optical pump pulses;*

*a compressor for compressing the amplified optical signal pulses to a time duration substantially shorter than the predetermined duration of said optical pump pulses; and*

*an application unit receiving an output of said compressor and applying said output to a specified location.*

*11. An optical pulse amplification and delivery system, comprising:*

*a pump source generating optical pump pulses of a predetermined duration;*

*a signal source generating optical signal pulses;*

*combining elements receiving and combining the optical pump pulses and the optical signal pulses, and providing combined optical pulses which are substantially temporally overlapped;*

*an amplifier including a non-linear crystal receiving the combined optical pulses and amplifying the optical signal pulses using energy of the optical pump pulses; and*

*a compressor for compressing the amplified optical signal pulses to a time duration substantially shorter than the predetermined duration of said optical pump pulses.*

*12. The optical pulse amplification system of claim 10, wherein said signal source comprises:*

*a signal pulse generator; and*

*a stretcher receiving and stretching signal pulses generated by the signal pulse generator.*

*13. The optical pulse amplification system of claim 11, wherein said signal source comprises:*

*a signal pulse generator; and*

*a stretcher receiving and stretching signal pulses generated by the signal pulse generator, to a duration approximating said predetermined duration.*

*14. The optical pulse amplification system of claim 11, wherein said compressor comprises a diffraction grating pair.*

* * * * *